United States Patent [19]

Barree

[11] Patent Number: 4,679,421
[45] Date of Patent: Jul. 14, 1987

[54] AUTOMATED GAS-LIQUID RELATIVE PERMEAMETER

[75] Inventor: Robert D. Barree, Littleton, Colo.

[73] Assignee: Marathon Oil Company, Findlay, Ohio

[21] Appl. No.: 884,252

[22] Filed: Jul. 10, 1986

[51] Int. Cl.$^4$ ............................................. G01N 15/08
[52] U.S. Cl. ......................................................... 73/38
[58] Field of Search ............................................. 73/38

[56] References Cited

U.S. PATENT DOCUMENTS

| | | | |
|---|---|---|---|
| 3,030,801 | 4/1962 | Allen | 73/38 |
| 3,199,341 | 8/1985 | Heuer, Jr. et al. | 73/38 X |
| 4,555,934 | 12/1985 | Freeman et al. | 73/38 |

OTHER PUBLICATIONS

W. W. Owens, D. R. Parrish, and W. E. Lamoreaux, "An Evaluation of a Gas Drive Method for Determining Relative Permeability Relationships", Petroleum Transactions, AIME, vol. 207, 1956, p. 275-280.
Lefebvre DU Prey, E., "Measure Des Permeabilities Relatives Par La Methode De Welge", Sep.-Oct., 1973, Revue De L'Institut Francais DU Petrole, p. 695-715.
S. C. Jones and W. O. Roszelle, "Graphical Techniques for Determining Relative Permeability from Displacement Experiments", Jour. of Petroleum Technology, May 1978, p. 807-817.
Literature References for Specifications of Commercially Available Apparatus.

Primary Examiner—Stewart J. Levy
Assistant Examiner—Joseph W. Roskos
Attorney, Agent, or Firm—Jack L. Hummel; Rodney F. Brown

[57] ABSTRACT

An automated system for instantaneously measuring the production rates of gas and liquid produced from a sample core for automatically determining gas-liquid relative permeability. An apparatus is provided for collecting the produced fluids wherein the weight of the produced liquid is monitored instantaneously by a sensitive electronic load cell and wherein the volume of the gas produced is instantaneously monitored.

34 Claims, 34 Drawing Figures

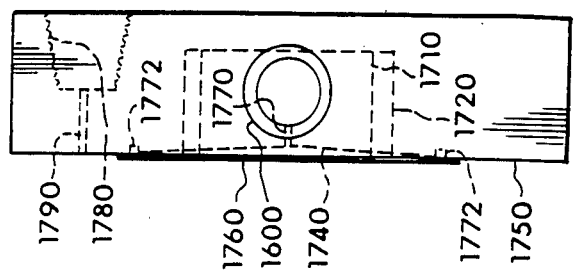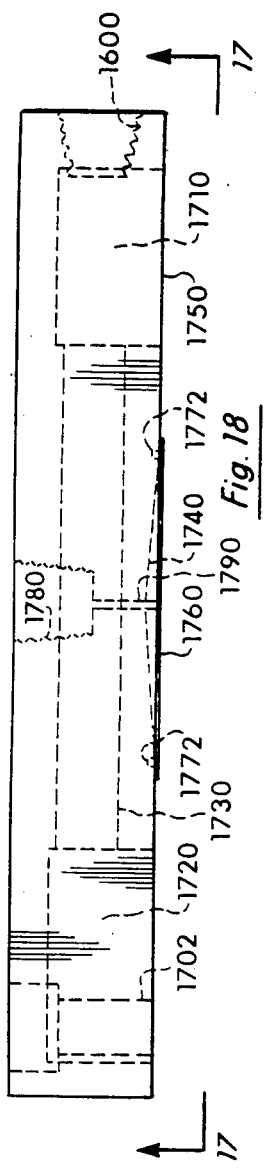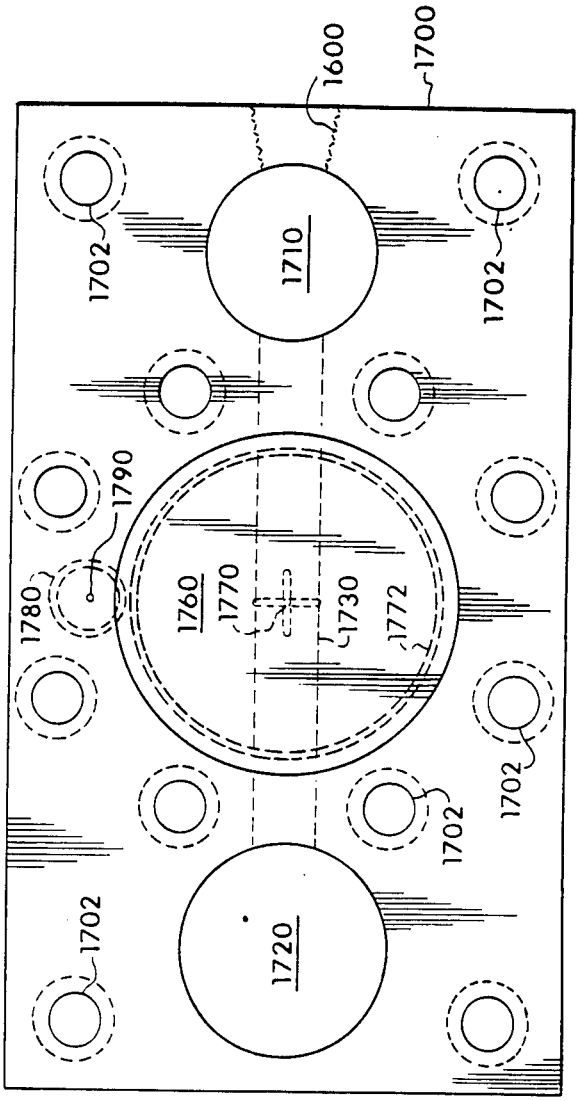

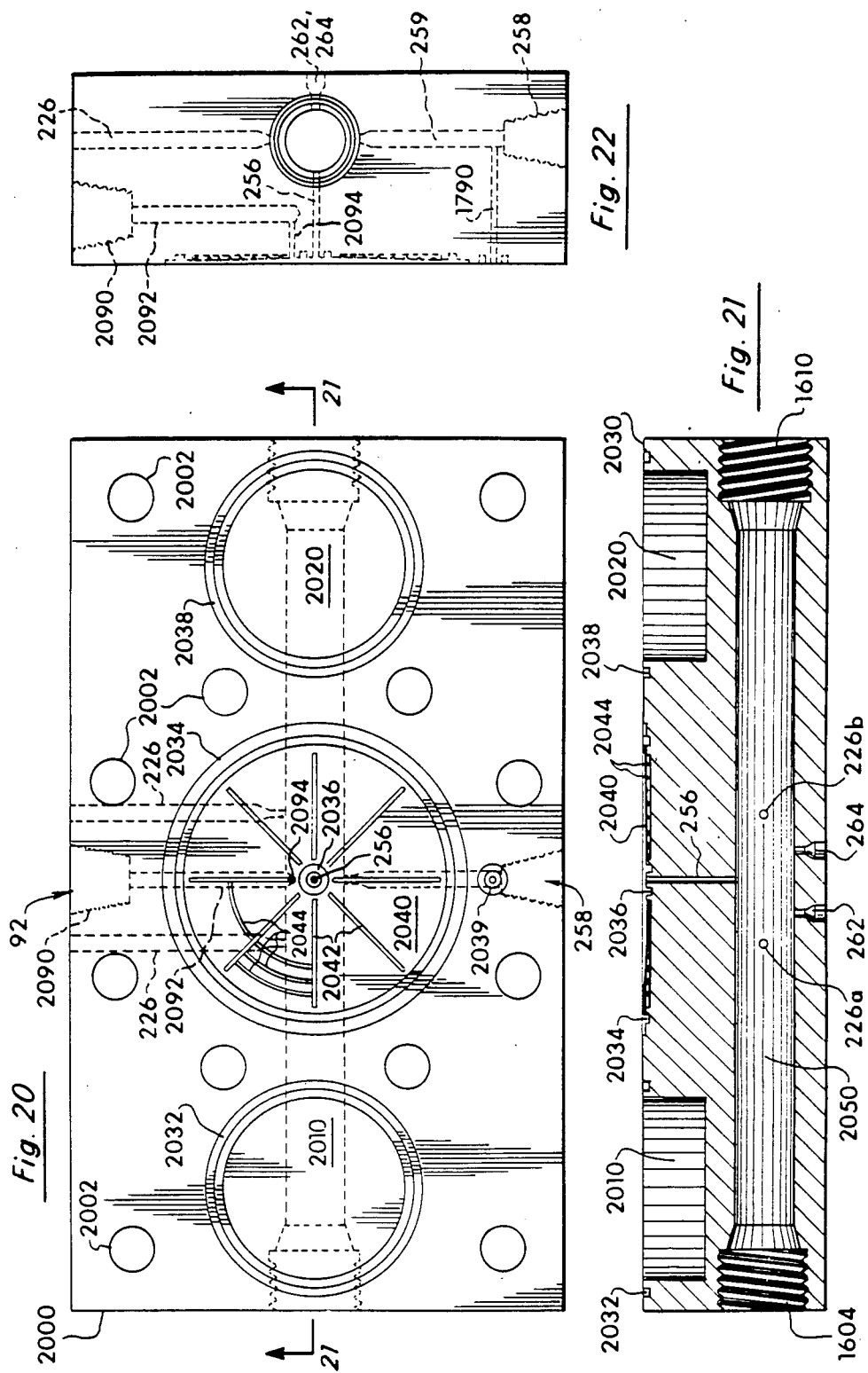

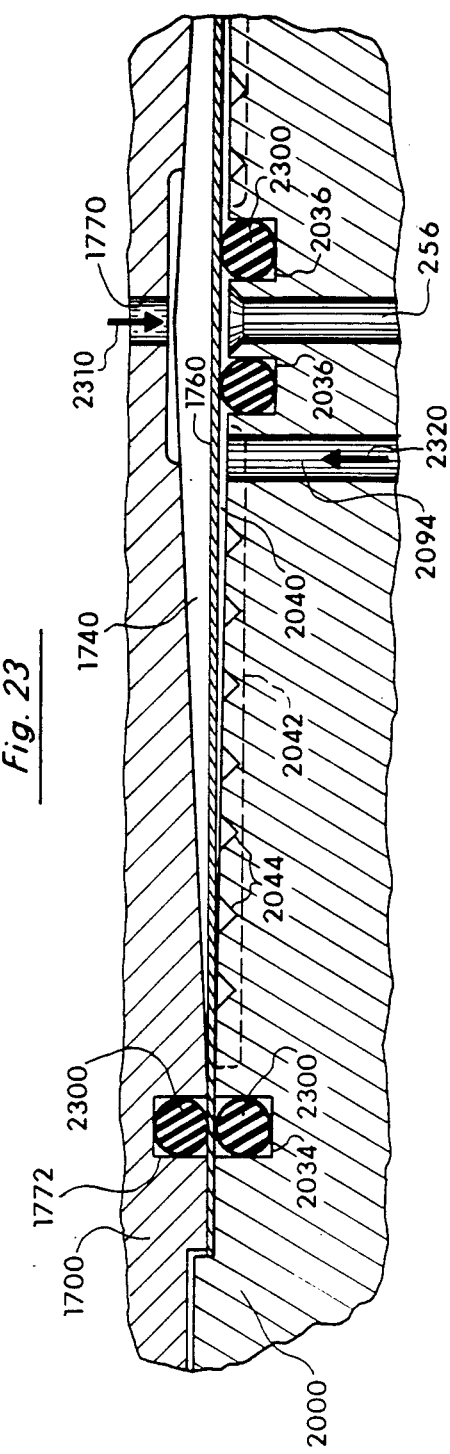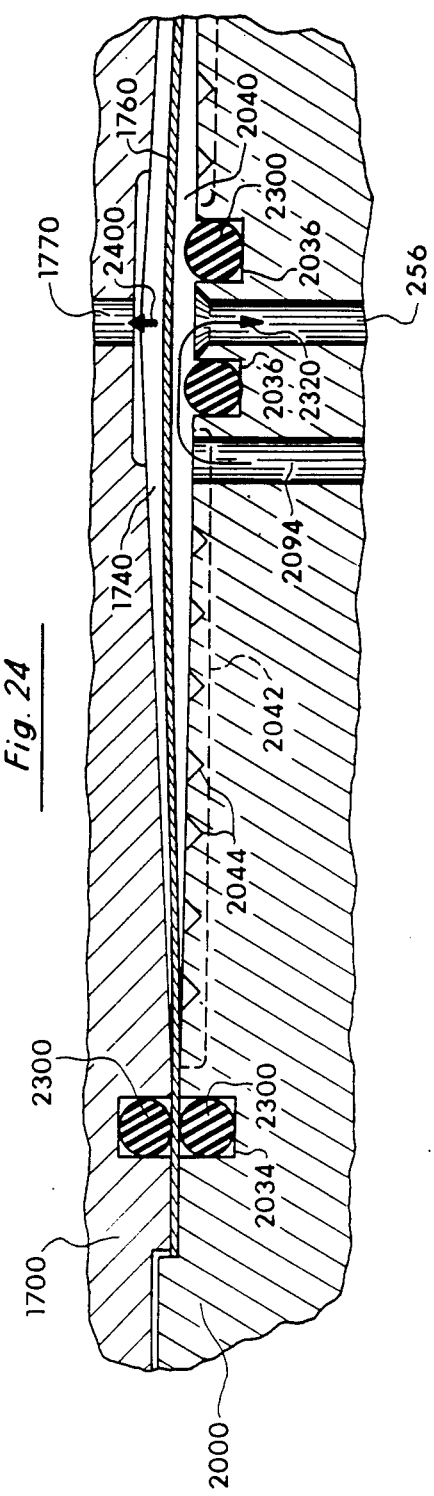

FLOW CHART OF REL-PERM CALCULATION PROGRAM

AUTOMATED GAS-LIQUID RELATIVE PERMEAMETER

BACKGROUND OF THE INVENTION

1. Field of the Invention

The present invention relates to a system and method for automatically determining gas-liquid relative permeability of liquid saturated core samples.

2. Discussion of the Background of the Invention:

One important consideration in evaluating reservoir characteristics of oil fields relates to a determination of the gas-liquid relative permeability of core samples from such reservoirs. Determination of such permeability figures are important in those oil fields producing by gas cap expansion, gravity drainage, solution gas, or injected gas drive.

Jones and Roszelle in "Graphical Techniques for Determining Relative Permeability From Displacement Experiments", May, 1978, Journal of Petroleum Technology, set forth various graphical techniques for rapidly and yet accurately determining gas/liquid relative permeability. A discussion of the apparatuses necessary for producing raw data are conventional and are, for example, discussed in "Lefebvre DU Prey, E."; "Mesure Des Permeabilites Relatives Par La Methode De Welge", September–October, 1973; Revue De L'Institut Francais DU Petrole, pages 695–715 and in Owens, et al. "An Evaluation of a Gas Drive Method For Determining Relative Permeability Relationships", Petroleum Transactions (AIME), Volume 207, 1956, pages 275–280. In the Owens article, the author recognizes that a primary goal in oil production research laboratories is the design of a simple and inexpensive, yet reliable approach for measuring the gas-oil flow characteristics of reservoir rock samples. The article classifies experimental methods into the three classifications of steady state, stationary liquid method, and non-steady state method.

The present invention pertains to the non-steady state method wherein a gas such as helium is injected into the core sample causing displacement of the liquid within the core sample thereby resulting in a system of continually changing average saturation and saturation gradient. The non steady state method is also termed, by Owens, the "gas drive method." Owens sets forth an apparatus and procedure for performing the gas drive relative permeability measurements. Owens discloses a means for separating and measuring the produced oil and gas volumes wherein the oil is captured in an oil burette and the gas is captured in a gas burette.

The approach set forth by Owens and others for measuring gas-liquid relative permeability under the gas drive method is a lengthy process requiring constant monitoring. The produced liquid is manually read from a burette as set forth in the Owens reference or from a series of collection bottles.

SUMMARY OF INVENTION

One problem, therefore, in measuring "gas-liquid relative permeability" is to provide a system and a method that allows the data to be collected automatically, without operator supervision. The present invention solves the above problem by providing an automated system for instantaneously measuring the production rates of gas and liquid produced from a sample core.

The present invention includes an apparatus for collecting the produced fluids wherein the weight of the produced liquid is monitored by a sensitive electronic load cell. Volumes and rates are automatically calculated from the liquid density. The produced gas is automatically directed to closed collection tanks via an automatic switching valve. The pressure in the tanks is constantly monitored and the gas flow rate is calculated from the rate of pressure change using the ideal gas law. The present invention being automated substantially decreases the time involved in measuring a given core sample. Previous methods required from two to six hours of continuous monitoring to complete a measurement. The present method requires five to ten minutes of operator intervention, while the entire determination requires 20 minutes to two hours. More complete data sets are acquired in the shorter time due to the increased sensitivity of the produced fluid measurement system.

BRIEF DESCRIPTION OF THE DRAWING

FIG. 17 is a bottom planar view of the regulator top 1700 of the gas collection system 110 of FIG. 16;

FIG. 18 is a front planar view of the regulator top 1700 shown in FIG. 17;

FIG. 19 is a side planar view of the regulator top 1200 shown in FIG. 17;

FIG. 20 is a top planar view of the regulator bottom 2000 of the gas collection system 110 of FIG. 16;

FIG. 21 is a cross-sectional view of the regulator bottom 2000 shown in FIG. 20;

FIG. 22 is a side planar view of the regulator bottom 2000 shown in FIG. 20;

FIG. 23 shows the operation in partial cross-sectional view of the dome regulator 250 of the present invention in the closed position;

FIG. 24 shows the operation of the dome regulator 250 of the present invention in the open position;

GENERAL DESCRIPTION

Figure 1:
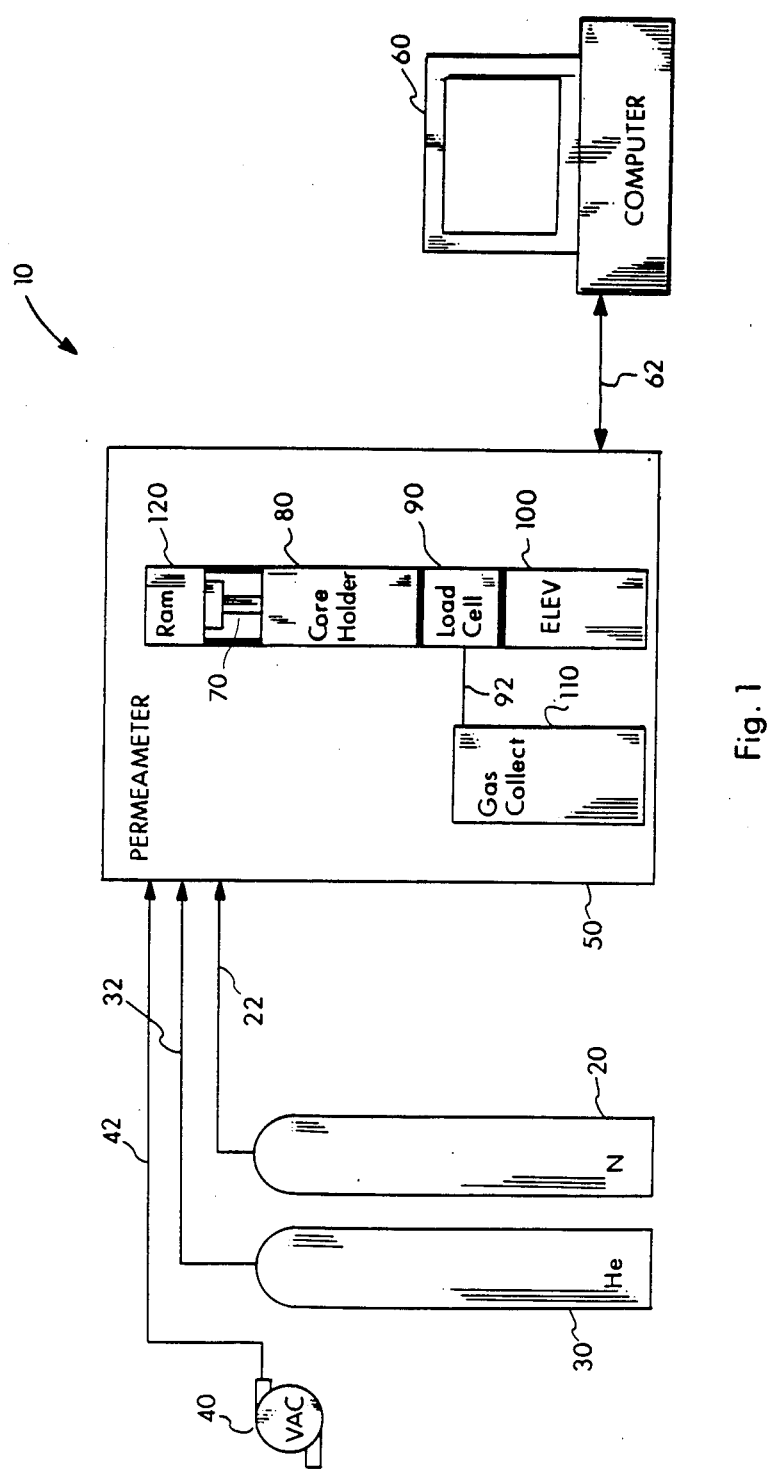
FIG. 1 is a block diagram illustration of the various components of the automated permeameter system of the present invention.

The system block diagram of the gas-liquid relative permeameter of the present invention 10 as shown in FIG. 1 includes a nitrogen supply 20, a helium supply 30, a vacuum 40, an automated permeameter 50, and a computer 60. The nitrogen supply 20 provides a pressurized supply of nitrogen over lines 22 to the permeameter 50. Preferably the pressure of the nitrogen supply 20 is 200 to 300 psig. The helium supply 30 provides a pressurized supply of helium to the permeameter 50 over lines 32. In the preferred embodiment, the helium supply 30 is pressurized to 150 psig. Finally, the vacuum 40 provides a selective vacuum over line 42 to the permeameter 50. The computer 60 provides data acquisition, control and display functions for the permeameter 50 and is connected thereto over lines 62. In the preferred embodiment, the computer 60 can be a conventional personal computer such as, for example, an IBM XT available from IBM Corp., P.O. Box 1328-W, Boca Raton, Fla. 33432.

Within the permeameter 50 are a number of elements which are generally shown in FIG. 1 to include a hydraulic ram 120, an inlet valve 70, a core holder 80, a load cell 90, an elevator 100, and a gas collection system 110. The load cell assembly 90 is interconnected to the gas collection system 110 over lines 92.

In operation, a sample core, not shown in FIG. 1, is held within the core holder 80. The sample core is fully saturated with liquid such as decane, Isopar-L or other mineral oil, or with an aqueous saline brine. When saturated it is ready for permeability testing. The core holder 80 is a conventional Hassler type core holder such as that available commercially from Temco, Inc., P.O. Box 51297, Tulsa, OK 74151. During core installation, the vacuum 40 delivers a vacuum over lines 42 to the core holder 80 to allow insertion of the core sample. Radial stress is then applied to the core by nitrogen pressure acting on an oil-filled pressure intensifier connected to the core holder. The hydraulic ram 120 applies the necessary axial stress to the core sample for testing. Pressures of 2,000 psi are typically obtained. Helium from supply 30 is delivered over lines 32 to the inlet valve 70 for injection into the core sample. The load cell assembly 90 is held up against the bottom of the core holder 80 by elevator 100. As the helium is delivered through the inlet valve 70 through the core sample and the core holder 80, the liquid generated from the core sample is collected in the load cell assembly 90. The weight of the liquid is automatically determined by computer 60 and the helium gas also produced is collected in the gas collection system 110 over lines 92. The pressure of the collected gas is likewise measured automatically by computer 60.

In general operation, the system of the present invention automatically monitors the volume of helium gas produced through the core sample as well as the weight of the liquid displaced. From this information the permeability of the core sample can be ascertained.

Figure 2:
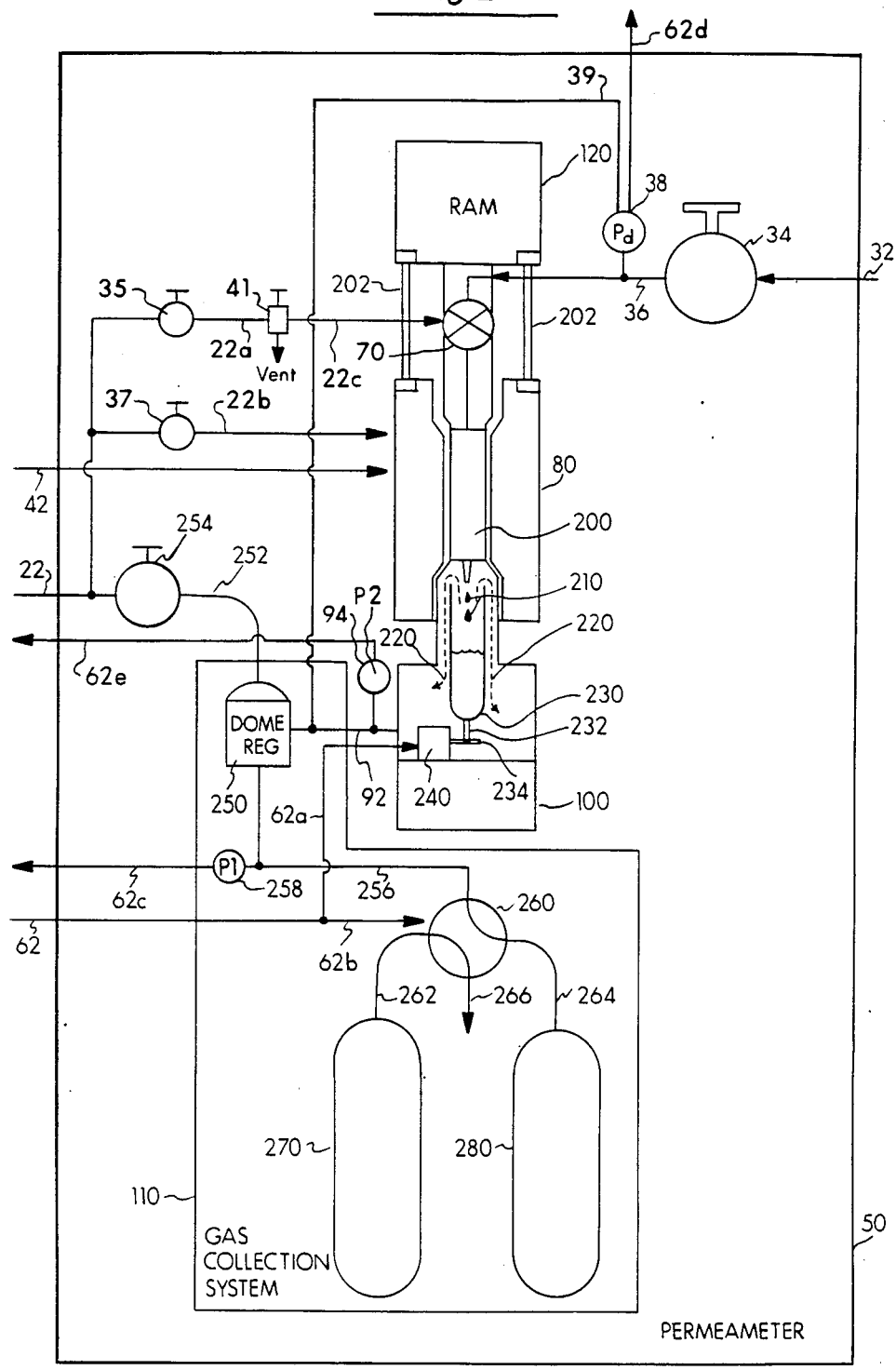
FIG. 2 is a block diagram showing the various components of the automated permeameter 50 of the present invention as shown in FIG. 1.

In FIG. 2, the block diagram for the permeameter 50 is set forth. In this diagram the hydraulic ram 120 and the elevator 100 are fully activated. The core sample 200 is pressurized and ready for testing. As shown in FIG. 2, the core sample 200 is mounted in the conventional Hassler core holder 80 and is held in place through pressure applied from the nitrogen source 20 over lines 22 through a pressure intensifier filled with mineral oil. The conventional pressure intensifier (not shown) is commercially available from High Pressure Equipment Co., Inc., 1222 Linden Avenue, Erie, PA 16505. The hydraulic ram 120 is connected to the core holder 80 by means of connection bolts 202. Disposed therebetween is the inlet valve 70 which contains a pneumatically operated piston. The inlet valve 70 is activated by the release of the nitrogen gas appearing in line 22a. Upon release of gas in line 22a, the valve 70 quickly activates to supply the helium in line 32 through pressure regulator 34 and through line 36 into the inlet valve 70. Between lines 36 and 92 is a pressure transducer 38 on lone 39 termed Pd. The pressure transducer 38 is capable of measuring the differential pressure Pd which will be discussed later. Hence, upon release of the nitrogen pressure in line 22b, inlet valve 70 becomes activated to provide helium gas from line 32 into the core holder 80 to the core sample 200. Nitrogen pressure on line 22a is controlled by a manually preset pressure regulator 35 at 150 psig. A second pressure regulator 37 directs nitrogen from supply 20 over line 22b to the pressure intensifier which activates the sealing of the sleeve in the core holder. Helium pressure on line 36 is typically 100 psi. When activated by manually turning the 3-way valve 41 to vent, the nitrogen pressure in Line 22c drops to 0 psig. The 3-way valve is a conventional type available from Whitey Co., 318 Bishop Rd., Highland Heights, OK 44143.

The pressurized helium flowing through the core sample 200 displaces the liquid contained therein and causes it to flow out as graphically illustrated by drops 210 in FIG. 2. The helium gas also flows out as indicated by arrows 220. The liquid 210 is collected in tube 230 which contains a pin 232 that rests on a lever 234 connected to a load cell 240. The load cell 240 in turn is connected over line 62a to the computer 60 which constantly monitors the weight of the displaced fluid in the tube 230. The helium gas 220 is delivered through line 92 to the gas collection system 110. Line 92 is in fluid communication with a dome regulator 250. A pressure transducer 94 measures the pressure of the helium gas in line 92. This pressure is denoted pressure P2. The dome regulator 250 is interconnected over line 252 to a pressure regulator 254 which is connected over line 22 to the nitrogen supply. The pressure regulator 254 provides a reference nitrogen supply to the dome regulator 250 so that when the pressure in line 92 exceeds a predetermined value, the dome regulator 250 becomes activated to deliver the helium in line 92 through line 256 to an automatic switching valve 260. The automatic switching valve is controlled by line 62b from computer 60. The helium delivered through line 256 is delivered either into tank 270 or into tank 280 over lines 262 and 264 respectively.

The computer monitors pressure transducers Pd over line 62d, and P2 over line 62e, along with the load cell 240 over line 62a. The automatic switching valve 260 over line 62b is activated when P1 reaches 95% of its full scale value (typically 10 psig).

The pressure in line 256 is monitored by a pressure transducer 258 which determines the helium pressure designated P1. The value of the pressure in transducer 258 is delivered over line 62c to the computer. Based upon this pressure reaching a predetermined value such as 9.5 psig, the computer 60 activates automatic switching valve 260 to deliver the helium gas into the other tank. When one tank is being filled, the other tank is being vented to atmosphere through vent 266. In this fashion, the precise amount of helium gas is collected, determined, and then vented.

As can be witnessed, instantaneous values of the fluid collected in tube 230 are determined and delivered to the computer 60 as well as instantaneous pressures existing in tanks 270 and 280. Furthermore, the collection of the fluid and gas, under the teachings of the present invention, are automated and greatly simplified over prior art approaches.

In summary, the general operation of the invention is shown in FIGS. 1 and 2. A core sample is conventionally saturated with liquid and contained within a conventional Hassler-type core holder 80. A vacuum is pulled on the core holder 80 to allow insertion of the sample. Stress is applied by the hydraulic ram 120 and by a pressure intensifier to the sleeve of the core holder. Hence, the core sample 200 is conventionally ready for permeability testing. The helium gas flows through pressure regulator 34 from helium tank 30 through the inlet valve 70 which consists of a pneumatically operated system. Inlet valve 70 becomes activated under control of the nitrogen supply 20 through line 22. This permits the helium gas to flow through the sample core 200 and to displace liquid 210. Under the teachings of the present invention, liquid 210 drops into a collection tube 230 which in turn rests on the cantilever beam of a load cell 240. The computer 60 of the present invention instantaneously records the weight of the displaced fluid in tube 230. Likewise, the helium gas 220 which is produced through the core sample 200 is delivered around the tube 230 and into a gas collection system 110. The produced helium gas is selectively delivered into one of two tanks 270 or 280 and instantaneous pressure in each tank is monitored. When a given tank is filled, the automatic switching valve 260 is activated to vent the filled tank and to fill the remaining tank. Since the tank pressure is monitored through pressure sensor 258, the computer 60 calculates the volume of the gas in the system at any given time. The elevator 100 selectively raises and lowers the load cell assembly 90 underneath the core sample 200 and core holder 80.

Hence, under the teachings of the present invention, by monitoring the differential pressure across the core (Pd), the down stream pressure (P2), the liquid weight from load cell 240, and the gas collection pressure (P1) throughout time, all data necessary to obtain gas-liquid relative permeability curves are acquired by the computer 60. By these measurements, the volumes of liquid and gas can be known at any time through application of the liquid density and Boyle's law. The rate of change of these qualities yields the instantaneous flow rates of oil and gas. Using the rates (and correcting the volumetric gas flow rate to average pressure in the core), the differential pressure, and the dimensions of the sample, the relative permeability curves are obtained by applying a numerical solution scheme based on the graphical technique of Jones and Roszelle (already cited).

DETAILED DESCRIPTION

In the following, the details of the inlet valve 70, the load cell assembly 90, and the gas collection system 110 will be set forth.

Inlet Valve 70

Figure 3:
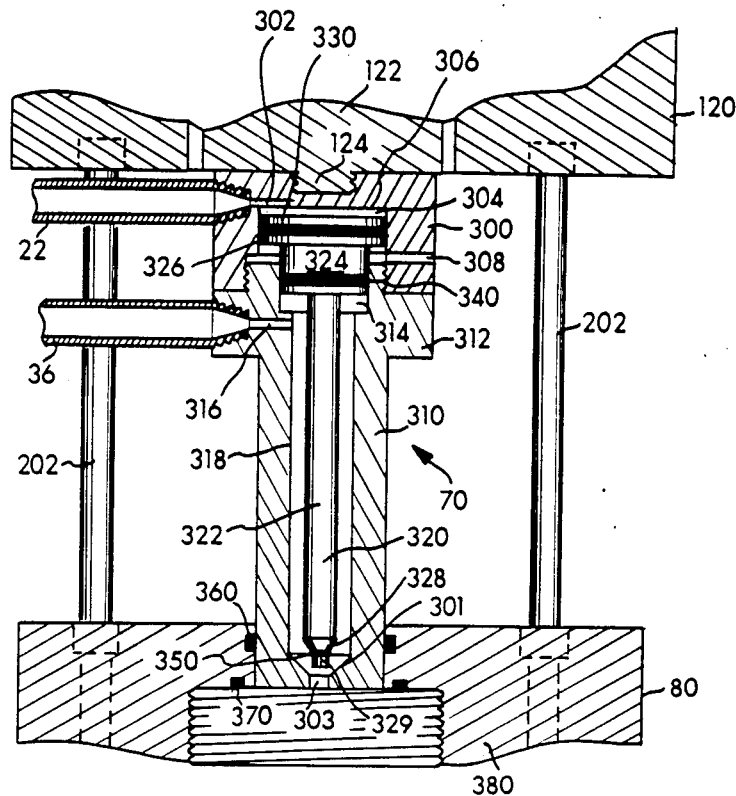
FIG. 3 is a cross-sectional view of the inlet valve 70 found in the automated permeameter 50 of FIG. 1.
Figure 4:
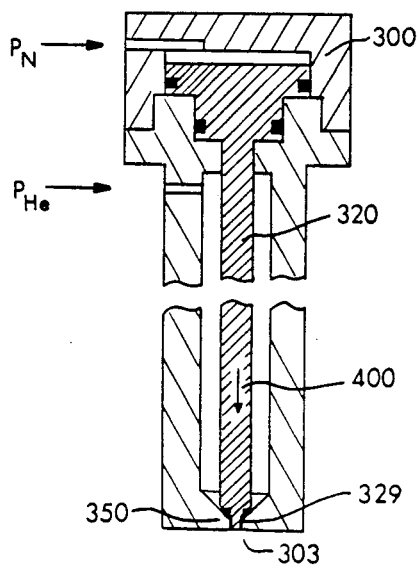
FIG. 4 is a partial cross-sectional view of the inlet valve 70 of FIG. 3 in the closed position.
Figure 5:
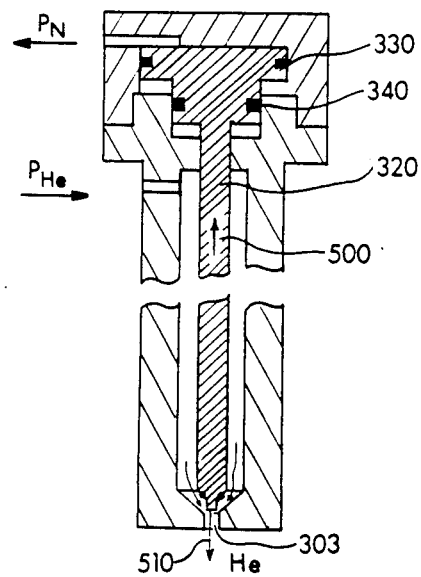
FIG. 5 is a partial cross-sectional view of the inlet valve 70 of FIG. 3 in the open position.

In FIGS. 3-5 are shown the details of the inlet valve 70 of the present invention. The inlet valve 70 of the present invention as shown in FIG. 3 has a cap 300, a body 310, and a piston 320. Connected to the cap 300 is the hydraulic ram 120 which is conventionally available such as from FABCO, Gainsville, Fla. 32601. The ram 120 has a hydraulic piston 122 which threadedly engages the cap 300 at point 124. The nitrogen line 22 also connects to the cap 300 and is in fluid communication with a formed port 302. The cap 300 is circular in shape and has an inner-formed cavity 304 which is cylindrical in shape. The port 302 communicates with the upper face 306 of the formed cavity 304. Finally, the cap 300 has a second formed port 308 which establishes fluid communication between the lower portion of chamber 304 and atmosphere. Threadedly connected to the cap 300 is the upper end of body 310.

The upper end 312 of body 310 has an enlarged diameter equal to the diameter of the cap 300. Formed in the upper end 312 is a cavity 314 cylindrical in shape and of lesser diameter than cylindrical cavity 304. Disposed below the lower end of cavity 314 is a formed port 316 which is in fluid communication with helium line 36 by means of a threaded engagement with upper end 312 of body 310. The upper formed cavity 314, at its lower end, terminates in a second formed elongated cylindrical cavity 318 of lesser diameter than formed cavity 314. Cavity 318 extends downwardly towards the bottom of body 310 into a region of an inwardly directed taper 301. The region of taper 301 then terminates into a downwardly extending port 303 to the exterior of the body 310.

As shown in FIG. 3, the piston 320 is disposed in cavities 304, 314, and 318. The piston 320 has a shaft 322 having connected at its upper end a first head 324 and on top of head 324 a second head 326. The diameter of piston head 326 is slightly less than the diameter of cylindrical cavity 304. The diameter of piston head 324 is slightly less than the diameter of formed cylindrical cavity 314. The diameter of the shaft 322 is much less than the diameter of cavity 318. At the bottom end of the shaft 322 is formed an inwardly conically-shaped tapering region 328 which terminates in a downwardly extending cylindrical plug 329. Disposed around the upper head 326 is a first O-ring 330. Disposed around the second piston head 324 is a second O-ring 340 and disposed around the conical tapered region 328 is a third O-ring 350.

The lower end of body 310 slip-fittingly engages the Hassler core holder 80. O-rings 360 and 370 provide a fluid seal between the cap 380 of the Hassler core holder body 80 and the body 310. A series of two bolts 202 firmly hold the entire assembly together between the hydraulic ram 120 and the Hassler core holder 80.

As shown in FIGS. 4–5, the inlet valve 70 of the present invention functions to rapidly inject helium gas into the top surface of the core sample 200. This occurs as follows. In FIG. 4, the nitrogen pressure $P_N$ is greater than the helium pressure $P_{He}$. This causes the piston 320 to move downwardly in the direction of arrow 400 to seal port 303 with plug 329. The O-ring 350 provides a solid fluid seal. Upon release of the nitrogen pressure to a value lower than the helium pressure, as shown in FIG. 5, the helium pressure causes the piston 320 to move upwardly in the direction of arrow 500 to open prot 303 and to let helium shown by arrows 510 to travel through to the upper surface of the core sample 200. The piston 320 moves quickly, opening the helium flow channel in times of several milliseconds.

Referring back to FIG. 3, port 308 provides atmospheric pressure to the region around piston 324 between O-rings 330 and 340 to allow free movement of the piston 320. O-rings 330 and 340 provide fluid seals so that the nitrogen and helium gases do not escape to the atmosphere.

While the above represents a preferred embodiment of the present invention for the inlet valve 70, it is to be expressly understood that other configurations for this valve either mechanical, as shown, or electrical could be utilized according to the teachings of the present invention.

Load Cell Assembly Mechanism 90

Figure 6:
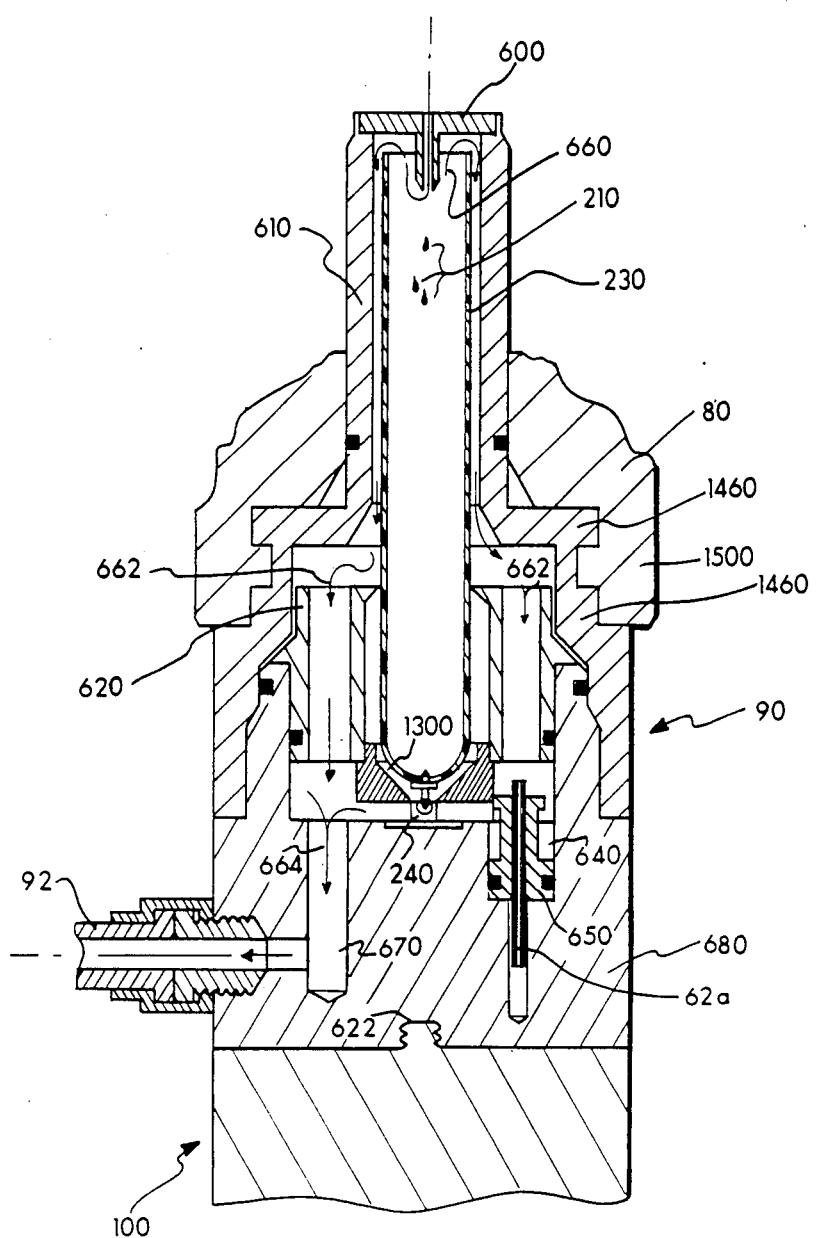
FIG. 6 is a cross-sectional vew of the load cell assembly 90 found in the automated permeameter 50 of FIG. 1.

In FIG 6, the load cell assembly mechanism 90 engages the Hassler core holder 80 on its upper end and the elevator 100 on its lower end.

The load cell assembly mechanism 90 includes a fluid outlet tube 600, a collection tube 230, and a core holder outlet 610 which engages with the Hassler core holder. Disposed within outlet 610 is the collection tube 230 and the tube support 620. Connected to the lower end of the core holder outlet 610 is the load cell cup 680. The load cell cup 680 is interconnected with helium outlet line 92 which, as shown in FIG. 2, connects with dome regulator 250 and provides an outlet, not shown, for wires 62a which are delivered to the computer as shown in FIG. 2. The load cell 240 is positioned in the center of the load cell cup 680 and below the bottom of the collection tube 230. To one side in a formed cylindrical cavity 640 is the electronics packaye 650 for load cell 240.

In operation, the helium gas which is delivered through the core 200 and through the fluid outlet tube 600 is delivered in the direction of arrows 660 around the external periphery of the collection tube 230 downwardly as shown by arrows 662 and into a formed cavity 670 as shown by arrow 664. It is then delivered from the load cell assembly mechanism 90 into lines 92.

In the configuration shown in FIG. 6, the elevator 100 is holding the load cell assembly mechanism upwardly to engage the Hassler core holder 80 so that the system can collect the fluids and the produced helium gas. As the gas is produced, fluid 210 is displaced and dropped into the collection tube 230. The collection tube 230 rests on the load cell 240 and its weight is instantaneously and automatically monitored for the duration of the testing period by computer 60 over lines 62a. Upon completion of the test, the elevator 100 is lowered and the load cell cup 680 including the tube support 620 and the collection tube 210 are removed from the core holder outlet 610.

Figure 7:
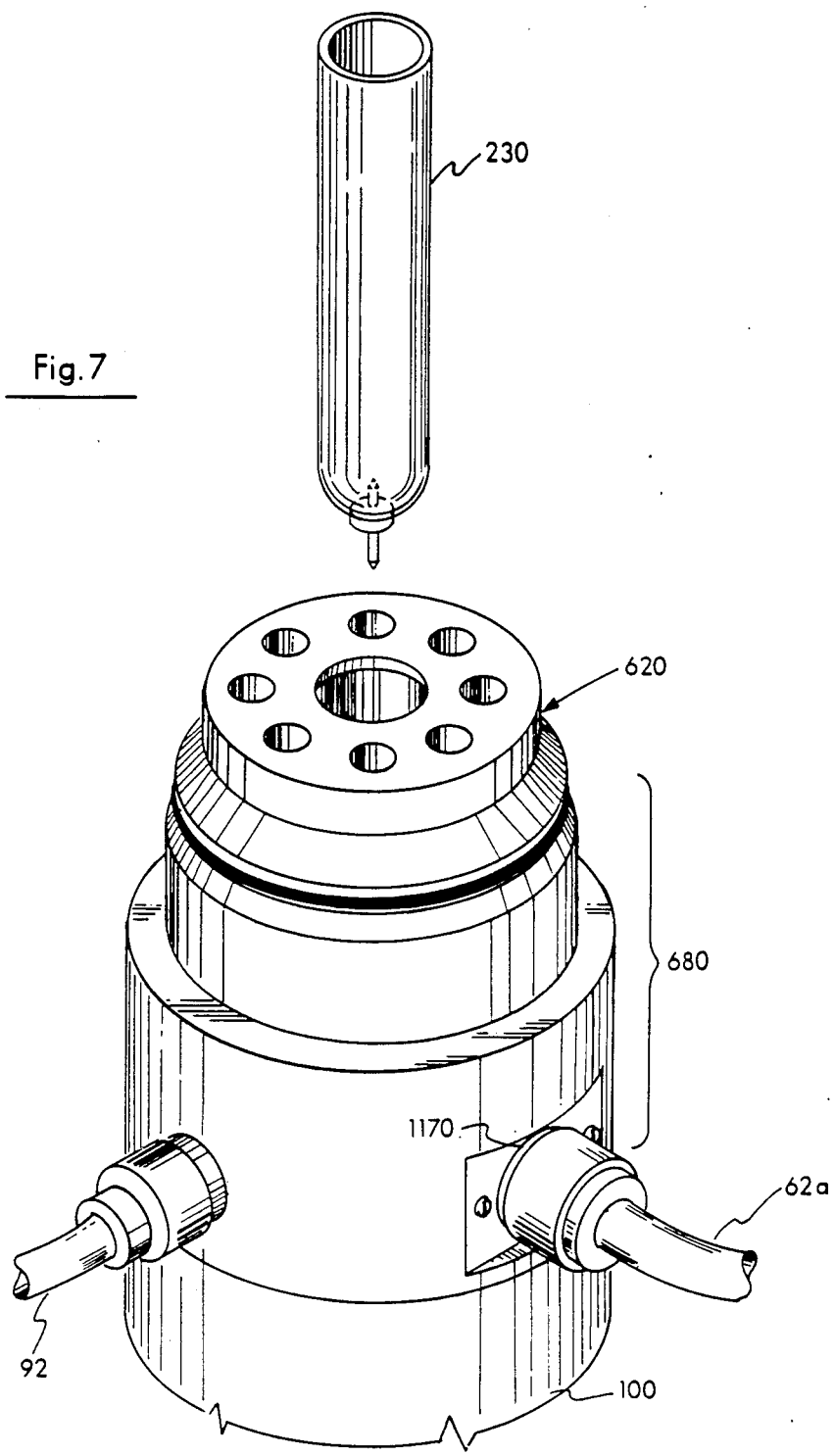
FIG. 7 is a perspective view of the load cell assembly 90 mechanism shown in FIG. 6.

This is more clearly shown in FIG. 7 where the elevator 100 is in the lowered position, load cell cup 680 being threadedly engaged at point 611 is also lowered. The helium line 92 is flexible and as shown in FIG. 7, also lowered. The tube support 620 press-fittingly engages the load cell cup 680 and is also lowered. In the lowered position, the collection tube 230 can be removed from the tube support 620 and cleaned of the collected fluid. The wires 62a are also shown in FIG. 7 which communicates with the computer 60.

Figure 8:
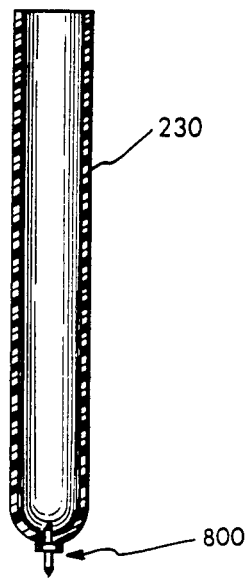
FIG. 8 is a side planar view of the collection tube 30 found in the load cell assembly 90 shown in FIG. 6.
Figure 9:
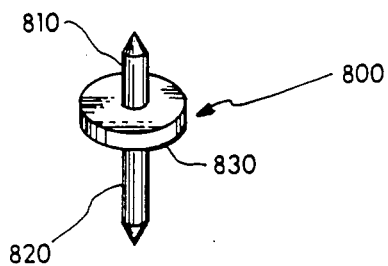
FIG. 9 is a perspective view of the collection tube pin 800 attached to the collection tube 230 shown in FIG. 8.

The details of the collection tube 230 are shown in FIGS. 8 and 9 to include a polyproplyene tube 230 having a pin 800 inserted through the bottom end. The pin 800 is shown in FIG. 9 to have an anchor end 810 and a bearing pin end 820. A collar 830 is disposed approximately around the mid-section of the pin. The pin 800 is driven into the bottom end of the polypropylyene tube until the collar 830 abuts the bottom of the tube 230. The bearing pin 820 engages the load cell 240 as will be subsequently explained. Leakage of collected fluid from the tube 230 is prevented by an epoxy resin cement bonding the pin 800 to the base of the tube.

Figure 10:
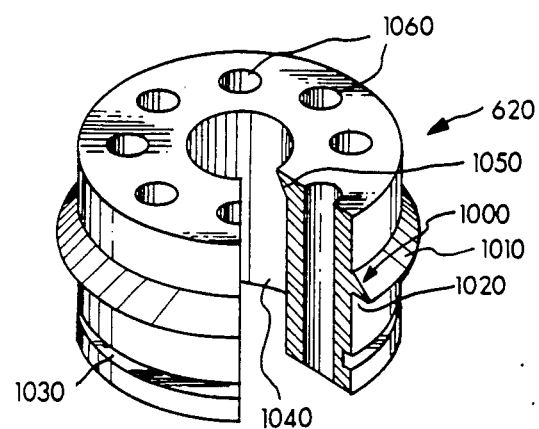
FIG. 10 is a perspective view, in partial cut-away, of the tube support 620 found in the load cell assembly 90 shown in FIG. 6.

In FIG. 10, the details of the tube support 620 are set forth. The tube support 620 is substantially cylindrically shaped with an outer lip 1000 formed around its periphery. The lip 1000 has a region of taper 1010 which terminates in a horizontal collar 1020. Disposed below the lip 1000 also on the outer periphery near the bottom of the support 620 is an O-ring notch 1030. In the center of the support 620 is an annular region 1040 through which the tube 230 passes. At the upper end of the support 620 is an inwardly directed region of taper 1050 which narrows to substantially equal the outside diameter of the collection tube 230. This region provides centering for the tube 230 when mounted in place. Disposed around the annular region 1040 are a number of cylindrical passageways 1060 which provide passage for the helium gas as shown by arrow 662 in FIG. 6.

Figure 11:
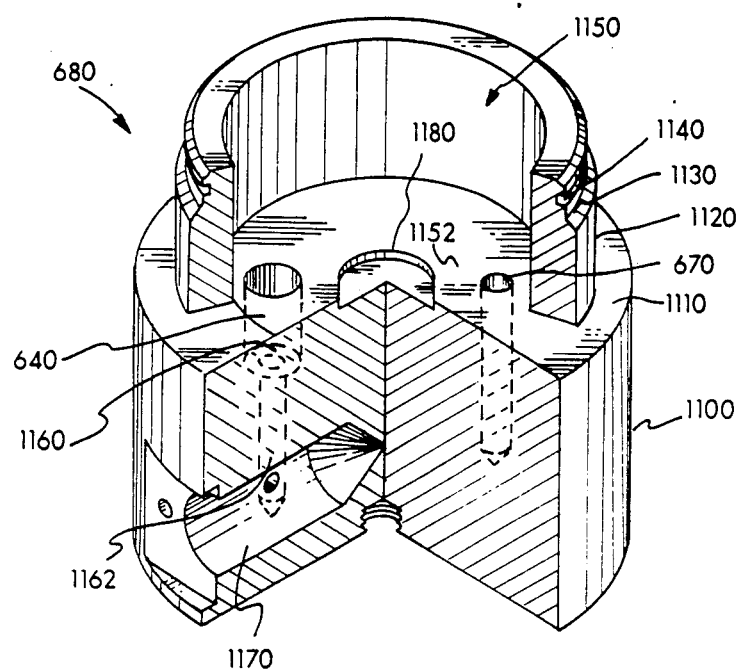
FIG. 11 is a perspective view, with partial cut-away, of the load cell cup 680 found in the load cell assembly 90 shown in FIG. 6.

The details of the load cell cup 680 are shown in FIG. 11. The cup 680 has a cylindrical bottom base 1100 terminating at the upper end in a circular ledge 1110. A second cylindrical region 1120 extends upwardly from ledge 1110 and then tapers through region 1130 to the cylindrical region carrying an O-ring notch 1140. A cylindrical cavity 1150 is formed in the top center of the load cell cup 680. As previously discussed, passageway 670 is disposed on the bottom internal face 1152 of cavity 1150 and it is located off center to one side. Line 92 is not shown in this view. Opposite the formed passageway 670 is the formed cavity 640 having a first region 1160 of greater diameter and a second region downwardly extending further 1162 of significantly less diameter. Region 1160 is designed to carry electronics package 650 for the load cell 240. The wires from the electronic package 650 are disposed downwardly into cavity 1162 which are then delivered through passageway 1170 out from the load cell cap 680. Disposed in the center of lower face 1152 of cavity 1150 is an oval shaped indent 1180 having one end located in the center of cavity 1150 and the second end extending towards one side of cavity 1150. The indent 1180 is designed to locate and center the load cell 650.

Figure 12:
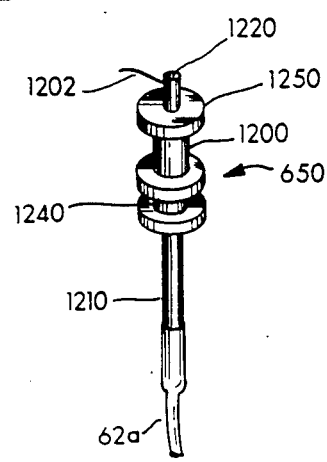
FIG. 12 is a perspective view of the electronics package 650 of the present invention.

The details of the electronics package 650 are shown in FIG. 12. Electronics package 650 includes a carriage 1200 and the housing 1210 for the electronics. The electronics housing 1210 is disposed internally in a formed annular region 1220 of the carriage 1200 and has an electrical connection 62a at one end and an electrical connection 1202 at the opposing end for connection to the load cell 240. Housing 1210 press-fittingly engages the annular region 1220 to which it is bonded with epoxy. The carriage 1200 is a formed cylindrical piece having an O-ring channel 1240 at one end and a lip 1250 at the opposing end. The lip 1250 allows for extraction of the electronics package 650 from the cavity 640 into which it is pressed during operation.

Figure 13:
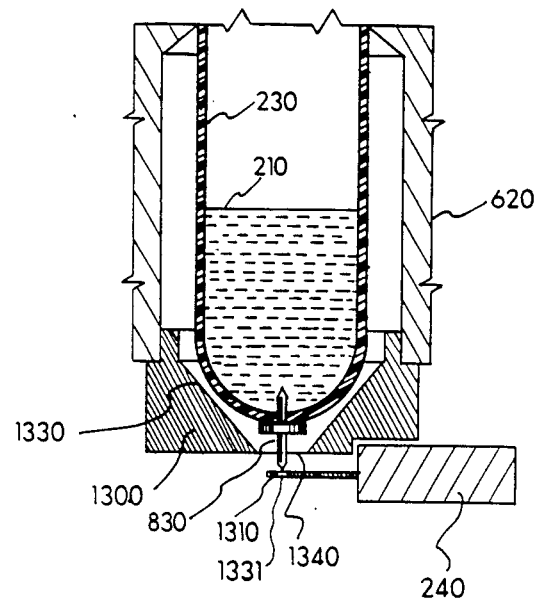
FIG. 13 is a partial cross-sectional view of the interaction of the collection tube 230 and the load cell 240 of the present invention.

In FIG. 13, the details of the guide cap 1300 are shown. The guide cap 1300 press-fits into the bottom of the tube support 620 so that when the tube 230 is in place, the bearing pin 830 extends through the bottom of the guide cap 1300 and abuts the cantilevered beam 1310 of the load cell 240 which is a conventional semiconductor strain gauge. The guide cap 1300 is circular in shape and fits into circular cavity 1040 of the tube support 620. The guide cap 1300 has inverted conical-shaped sides 1330 which are formed to correspond to the bottom end of the tube 230. In the center of the guide cap 1300 is an annular hole 1340 through which the pin 830 can travel.

Under the teachings of the present invention, the bottom of the tube 230 is guided by the edges of the conical shaped sides 1330 so that the pin is caused to rest in a hole 1331 in the end of the cantilever beam 1310 of the load cell 630. As the tube fills with liquid 210, the beam 1310 is moved in a downwardly direction and the load cell 630 instantaneously weighs the fluid 210.

The load cell 240 which has a preferred range of 0–10 grams is conventionally available from Kulite Semiconductor Products, Inc., 1039 Hoyt Avenue, Ridgefield, NJ 07657, Model No. BG-10.

It is important to note at this point that the collection tube 230 can be easily removed from load cell apparatus 90 when the elevator 100 is in the down position. The specific embodiment for accomplishing this is shown in FIGS. 7–13 and represents one preferred approach under the teachings of the present invention for accomplishing this approach. It is to be expressly understood that the invention, however, is not so limited and other structural approaches may be utilized to provide for the selective removal of the collection tube 230 from core holder 80 and from the load cell cup 680.

In addition, when the elevator 100 is in the loaded position as shown in FIG. 6, the structure of the present invention permits the collection of the liquid separate from the collection of the helium gas and provides for an accurate measurement of the collected fluid on an instantaneous and automatic basis. Again, it is to be expressly understood that the embodiment shown in FIGS. 6–13 represents the preferred embodiment and that other structural designs may be utilized to accomplish the same desired affect.

Figure 14:
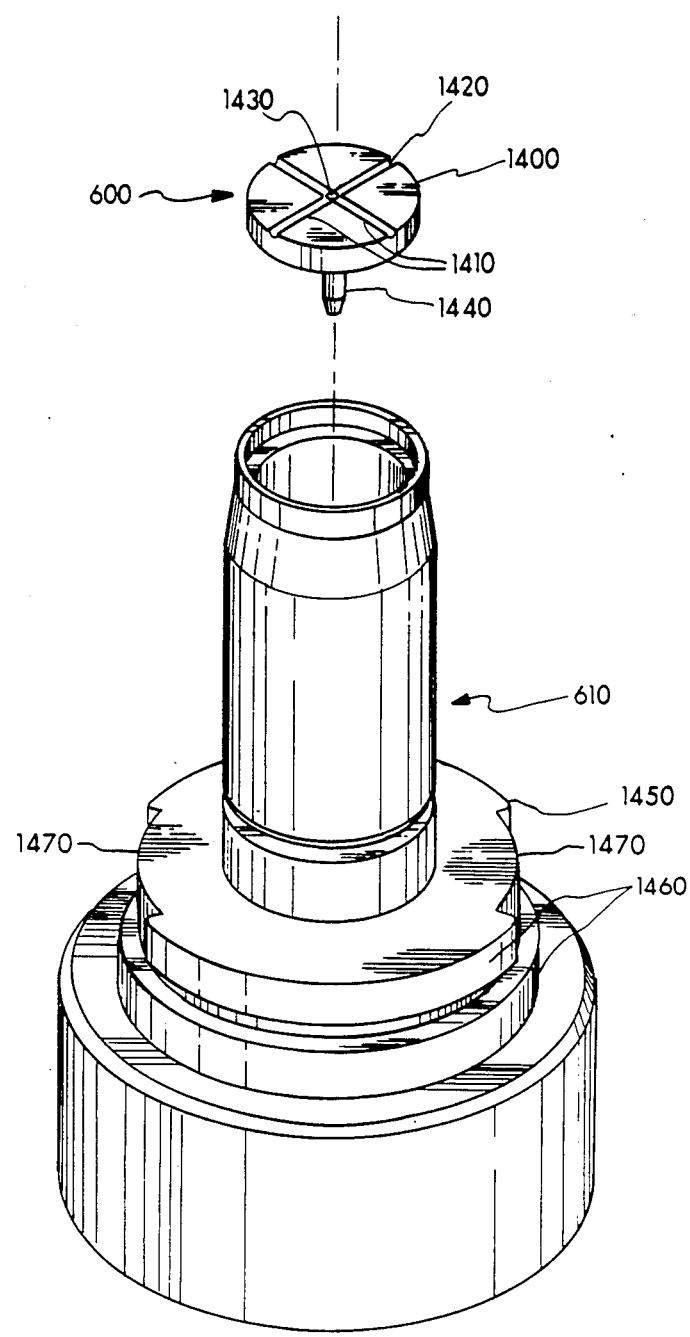
FIG. 14 is a perspective view of the core holder outlet 610 as shown in FIG. 6.
Figure 15A:
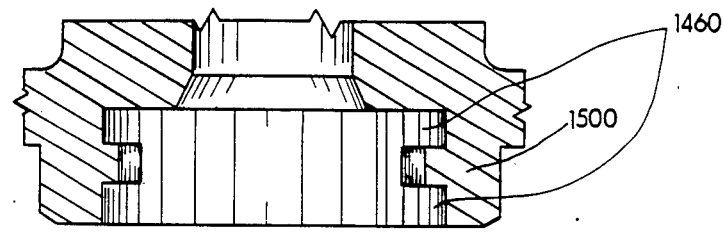
FIG. 15 is a bottom planar view of the Hassler core holder 80 as shown in FIG. 2 and 15a is a cross-sectional view along lines 15a—15a of FIG. 15.
Figure 15:
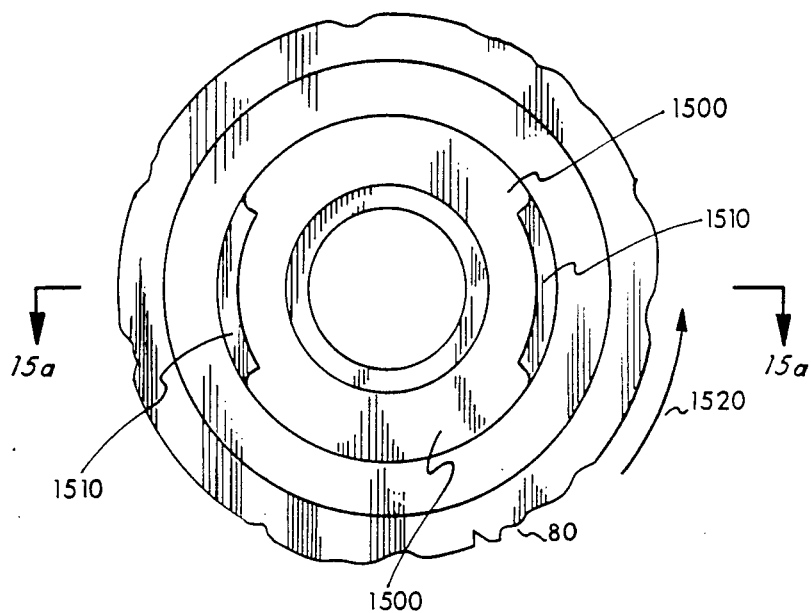

In FIG. 14 is a perspective view of the core holder outlet 610. Welded to the top end of the outlet 610 is the fluid outlet tube 600. The fluid outlet tube 600 is comprised of a top circular disk 1400 having a plurality of formed grooves 1410 for expediting the flow of the fluid and helium gas from the bottom surface of the core 200. The upper surface 1420 of the disk 1400 abuts the bottom end of the core sample 200. A formed passageway 1430 permits the helium gas and fluid to flow downwardly through tube 1440. As shown in FIG. 6, the location of the output of tube 1440 is directed into the collection tube and this is where the separation of the helium gas 660 from the liquid 210 occurs. Disposed on surface 1450 of outlet 610 are two opposing flanges 1460. These flanges 1460 engage mating flanges 1500 on the Hassler core holder 80 in order to provide a lock thereto. In the upper of the two flanges 1460 are cut cavities 1470, which fit over lugs 1510 shown in the bottom planar view of the conventional Hassler core holder 80 shown in FIGS. 15 and 15a. In FIG. 15, the core holder 80 has bottom flanges 1500 so that when the flanges 1460 of the outlet 610 are lifted over lugs 1510 and then twisted in the direction of arrow 1520, the outlet 610 firmly engages the Hassler holder 80. In this fashion, the outlet 610 can be easily removed from the Hassler core holder 80.

Gas Collection System 110

Figure 16:
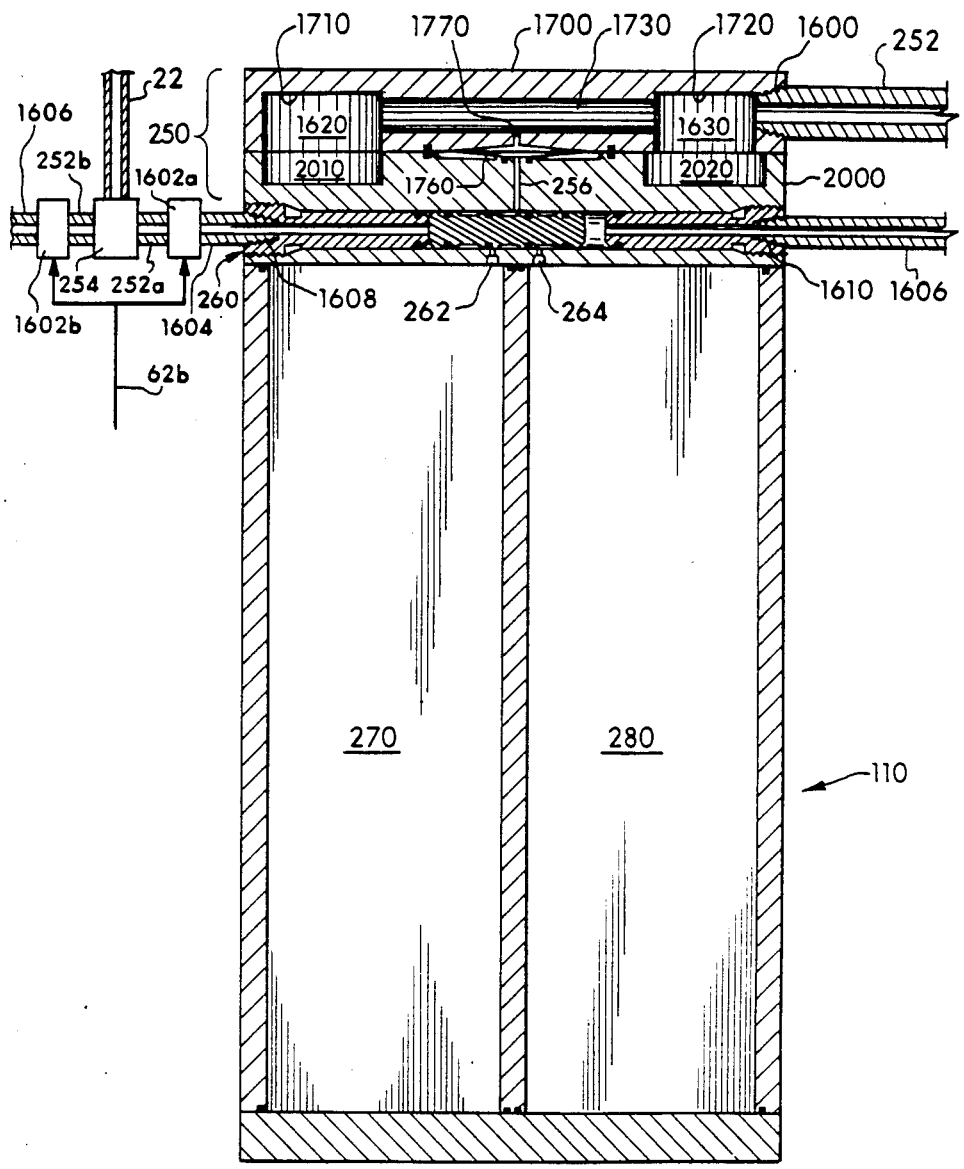
FIG. 16 is a cross-sectional view of the gas collection system 110 as shown in FIG. 2.

The details of the gas collection system 110 are shown in FIG. 16. The nitrogen line 252 delivered from the pressure regulator 254, as shown in FIG. 2, accesses the dome regulator 250 through a formed threaded port 1600. Nitrogen is delivered from line 22 through a manually preset pressure regulator 254 so that a nitrogen pressure of approximately 100 psig is delivered to an assembly of two electrically operated solenoid valves 1602. The solenoid valves 1602 are conventional such as those available from Skinner Valve Div., Honeywell, Inc., New Britain, Conn. The solenoid valves 1602 deliver the nitrogen gas from line 22 into either line 1604 or 1606 under control of the computer over lines 62b. Line 1604 accesses the automatic switching valve 260 through a formed threaded port 1608. Line 1606 accesses the opposite side of the automatic switching valve 260 through formed threaded port 1610. The solenoid valves 1602 are under electrical control over line 62b which is delivered to the computer. The appropriate signal on line 62b causes nitrogen pressure to be in either line 1604 or in line 1606 to activate the automatic switching valve 260 in a fashion to be subsequently described.

The nitrogen pressure in line 252 also provides a reference pressure to the dome regulator 250. When the helium pressure in the dome regulator 250 exceeds the referenced nitrogen pressure, the dome regulator 250 becomes activated and provides a passage for the helium gas into either tank 270 or tank 280 depending upon the position of the automatic switching valve 260. When the helium is flowing into one tank, such as for example tank 270, the remaining tank, such as tank 280, is vented to atmosphere. The details of the gas collection system 110 shown in FIGS. 2 and 16 will now be discussed.

The top 1700 of the dome regulator 250 is detailed in FIGS. 17 through 19. The top is machined preferably from aluminum material and it includes a number of drilled bolt holes 1702. Only one of the drilled holes 1702 is shown in FIG. 18 and none are shown in FIG. 19 for the convenience of clarity. Also machined are two cylindrical cavities 1710 and 1720. Cavity 1710 is of smaller diameter than cavity 1720. These form part of the dome spaces 1620 and 1240 as shown in FIG. 16. Interconnecting the two cavities 1710 and 1720 is a fluid pathway 1730. The threaded inlet 1600 for the nitrogen line 252 is also formed to communicate with cavity 1710. As shown in FIGS. 17 through 19, the fluid pathway 1730 is approximately in the center of the regulator top 1700 and is in line with the nitrogen formed inlet 1600.

A shallow cavity 1740 is formed on the lower surface 1750 of regulator top 1700. This shallow cavity 1740 is circular in shape and has affixed thereover a thin diaphragm 1760 suitably resting on an O-ring seal at point 1772 in the lower face 1750. A small port 1770 is drilled from the lower surface 1750 and the center of the regulator top 1700 upwardly and into the fluid pathway 1730. Hence, as shown in FIGS. 17 through 19, the incoming nitrogen through inlet 1600 and cavity 1710 and 1720 pressurize the fluid passageway 1730 and deliver a predetermined amount of pressure through port 1770 into the cavity 1740 underneath the diaphragm 1760 causing the diaphragm to extend downwardly against the upper surface of the regulator bottom 2000.

Threaded part 1780 connecting with hole 1790 is a connection for a spring loaded pressure relief valve, not shown in FIG. 2, of the type available from NUPRO Company, 4800 E. 345th Street, Willoughby, OH 44094. This relief valve, which connects to the pressure transducer port 258 in the regulator bottom 2000, acts to protect the pressure transducer (P1) 258 from damage in the event of a failure of the automatic switching valve.

The regulator bottom 200 is shown in FIGS. 20 through 22. The regulator bottom 2000 comprises the same shape as the regulator top and has correspondingly formed bolt holes 2002 which are only shown in FIG. 20. It is to be expressly understood that conventional bolts pass through the formed holes 2002 and 1702 to firmly hold the regulator top 1700 and to the regulator bottom 2000 to the gas collection tanks 270 and 280. The regulator bottom 2000 also has formed cylindrical cavities 2010 and 2020 which cooperate with cylindrical cavities 1710 and 1720 to form the dome spaces 1620 and 1630 as shown in FIG. 16. These formed cylindrical cavities 2010 and 2020 are formed in the upper surface 2030 of the regulator bottom 2000. Also formed in the upper surface 2030 are a plurality of O-ring slots 2032, 2034, 2036, 2038, and 2039. Conventional O-rings fit within these slots and when the regulator top 1700 is mounted to the regulator bottom 2000, an effective plurality of seals are obtained. Also formed in the upper surface 2030 is a shallow cavity 2040. In cavity 2040 are a plurality of radial slots 2042 and a plurality of circular grooves 2044 (only some of which are shown in FIG. 20). In the center of the formed cavity 2040 is a formed port which comprises line 256. Line 256, as shown in FIG. 2, is the line that connects the dome regulator 250 with the automatic switching valve 260.

In the lower portion of the valve bottom 2000 is a formed cylindrical passageway 2050. Threaded inlets 1604 and 1610 are at opposing ends of the passageway 2050. In fluid communication with passageway 2050 are ports 262 and 264 which correspond to lines 262 and 264 shown in FIG. 2 providing access to tanks 270 and 280 respectively as shown in FIG. 16. In addition, ports 226 are provided in the passageway 2050 which are ports venting to the atmosphere.

Also shown in FIGS. 20 through 22 is the helium input line 92 connected to a formed inlet 2090 for delivery of the helium gas into a formed passageway 2092 and then upwardly through passageway 2094 and into the formed cavity 2040 as best shown in FIG. 22. The pressure transducer P1 engages port 258 which in turn is in fluid communication with passageway 2050 and passageway 1790.

The operation of the dome regulator 250 will now be presented with reference to FIGS. 23 and 24. In FIG. 23, the regulator top 1700 is shown firmly engaging the regulator bottom 2000. O-rings 2300 are shown in slots 1772, 2034 and 2036. Formed shallow cavities 1740 and 2040 are also shown. In the position shown in FIG. 23, the incoming nitrogen gas 2310 (from chambers 1620 and 1240 of FIG. 16) applies sufficient pressure to the diaphragm 1760 to firmly hold it against the O-ring 2300 in slot 2036 to seal off port 256. In this mode of operation, the helium present in line 2094, as shown by arrow 2320, is contained within cavity 2040. No helium is delivered into passageway 256 due to the fluid seal produced by the diaphragm 1760 contacting the O-ring 2300 around port 256. However, when the developed pressure from the core sample 200 exceeds the predetermined value of nitrogen pressure 2310 in line 1770, diaphragm 1760 as shown in FIG. 24 is lifted upward in the direction of arrow 2400 thereby permitting the helium as shown by arrow 2320 to flow into passageway 256 and then into the tanks 270 or 280. The provision of the circular grooves 2044 and the radial slots 2042 in the lower cavity 2040 facilitate distribution of the helium present in line 2094 against the diaphragm 1760.

In this fashion, when the helium obtains a predetermined pressure such as 80 psig dome regulator of FIG. 2 becomes activated and delivers the collected helium from the core sample 200 into either tank 270 or tank 280 which is under control of the automatic switching valve 260. In operation, a space is maintained between diaphragm 1760 and O-ring 2300 in slot 2036 such that the resistance to flow of helium gas through the narrow gap thus formed causes the pressure of gas in cavity 2094 to remain constant at the desired value of 80 psig.

Figure 25:
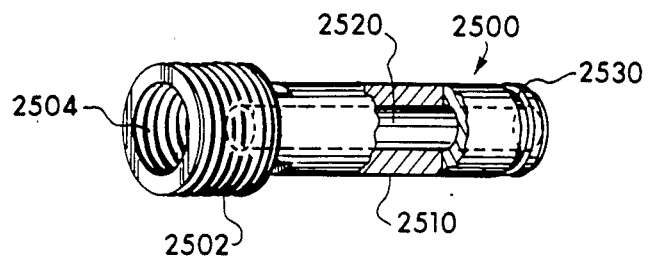
FIG. 25 is a perspective view of the valve plug 2500 of the present invention.
Figure 26:
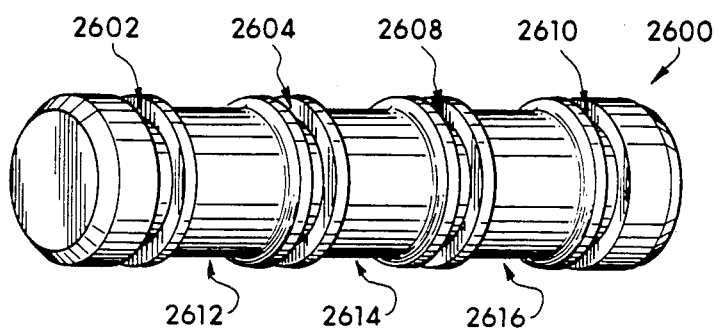
FIG. 26 is a perspective view of the spool 2600 of the present invention.

The details of the automatic switching valve 260 are shown in FIGS. 21, 25, and 26. Two valve plugs 2500 are inserted into the inlets 1604 and 1610 of the regulator bottom 2000. Each valve plug 2500 contains a threaded end 2502 with an inlet 2504 for receiving the nitrogen gas from either line 1604 or line 1606. The valve plug 2500 comprises a major cylindrical portion 2510 having a centrally disposed fluid passageway 2520 terminating in an end having an O-ring slot 2530 to which a conventional O-ring is affixed to provide a fluid seal as shown in FIG. 16.

Centrally disposed in passageway 2050 is a spool 2600. The spool as shown in FIG. 26 comprises four O-ring grooves 2602, 2604, 2608, and 2610 to which are attached conventional O-rings as shown in FIG. 16. Between the O-ring grooves 2602–2610 are three formed cavities 2612, 2614, and 2616.

Figure 27:
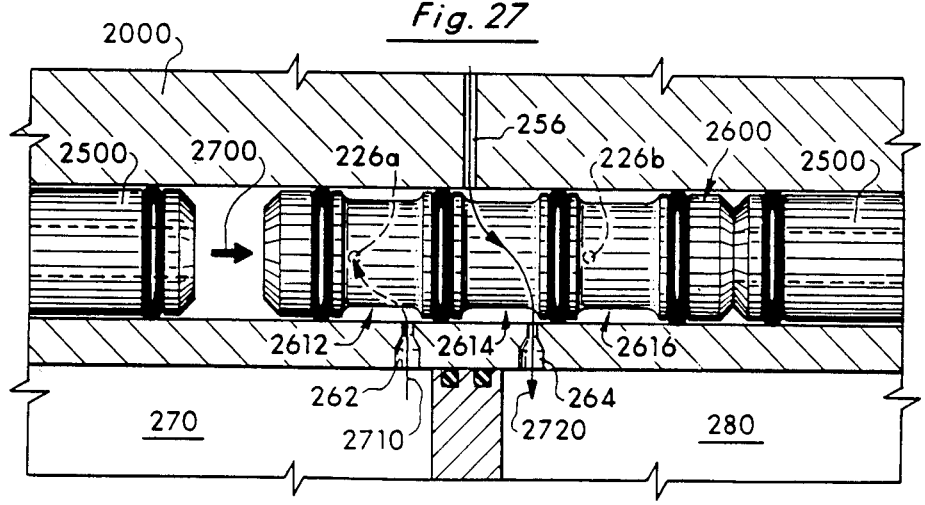
FIG. 27 is an illustration, in partial cross-section, showing the operation of the automatic switching valve 260 as shown in FIG. 2.

The operation of the automatic switching valve 260 is shown in FIG. 27. When the nitrogen pressure is delivered through line 1604, as shown in FIG. 16, the nitrogen as shown by arrow 2700, in FIG. 27, pushes the spool 2600 against the opposing valve end plug 2500. In this orientation, the helium gas in tank 270 is delivered as shown by arrow 2710 through port 262 around region 2612 of the spool 2600 and out through port 226a to atmosphere. At the same time, helium being delivered through port 256, as shown by arrow 2720, is delivered around region 2614 through port 264 into tank 280. In this mode of operation, the third region 2616 seals port 226b which is vented to atmosphere from the system. In like fashion, spool 2600 operates in the opposite direction to fill tank 270.

As shown in FIGS. 20 and 22, the pressure transducer P1 is connected to port 258 and passageway 259. Passageway 259 continuously accesses region 2614, regardless of the position of the spool 2600, to measure the instantaneous pressure of the tank being filled.

Operation of Automatic Permeameter System

Figure 28:
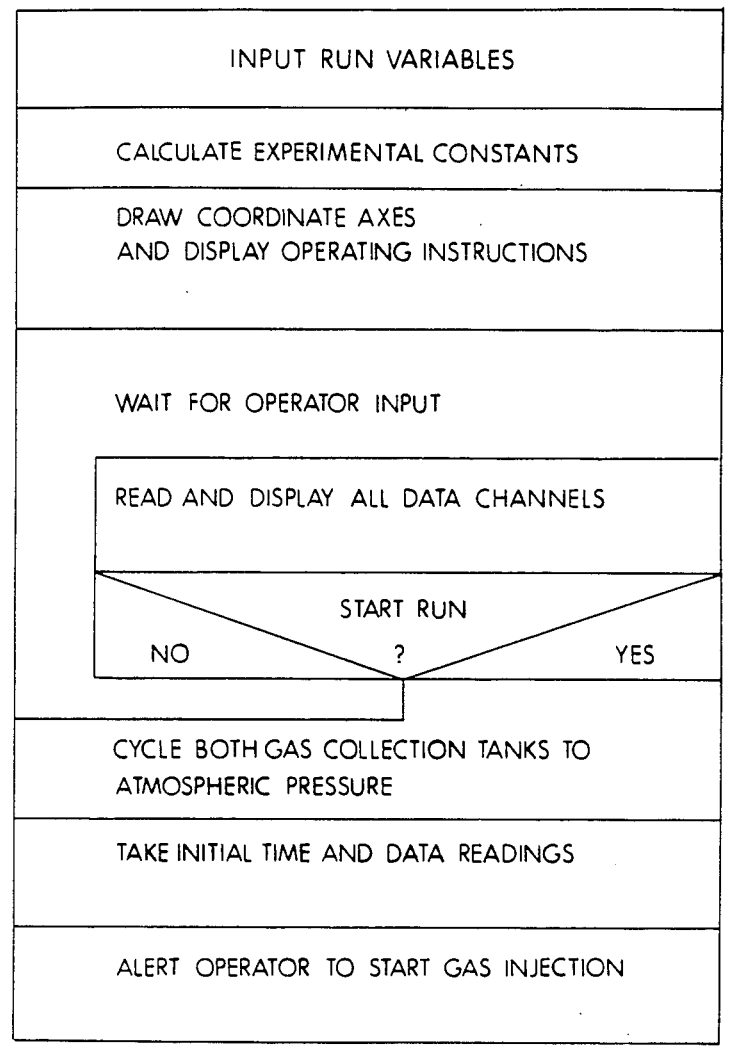
FIGS. 28 through 31 are flow charts setting forth the operation of the present invention.

The operation of the present invention is set forth in FIGS. 28 through 33. In FIG. 28, the operator manually inputs the testing variables into computer 60. Input variables include the core fluid properties, atmospheric properties, and other parameters of the core such as its length, diameter, porosity, and absolute permeability.

Computer 60 then calculates the experimental constants, draws a coordinate axis on the monitor and displays the operating instructions. It then waits for additional operator input. While waiting it reads and displays the data for all channels such as the pressure P1 in the tanks, the downstream pressure P2, the reading on the load cell, and the differential pressure PD across the core sample. It then waits for a start run signal. If none, it simply cycles and displays the data readings. If the operator starts the run, then it cycles both gas selection tanks 270 and 280 in order to vent both tanks to atmospheric pressure discussed in FIG. 27. In other words, the computer over line 62b selectively activates the automatic switching valve 260 to vent tanks 270 and 280 to atmospheric pressure. The computer takes initial time and data readings and then it alerts the operator to start gas injection.

Figure 29:
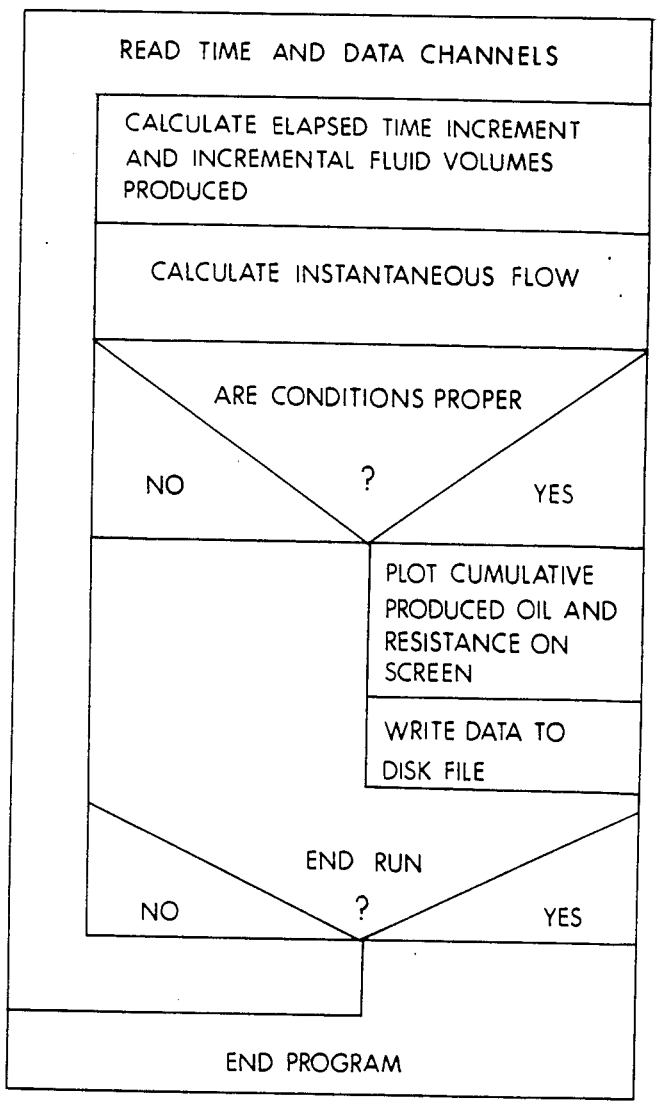

In FIG. 29, the computer 60 then reads the time and data channels 62a through 62e. Time is obtained from the internal system clock supplied with the computer 60. Data channels are read in a set order: pressure in tanks, P1; load cell indication, downstream pressure, P2; and differential pressure, Pd. The data is translated from analog (voltage) signals to digital signals by a commercially available interface card contained in the computer 60, such as Model SG04 manufactured by ICS, 8601 Aero Drive, San Diego, CA 92123. The computer 60 then calculates the elapsed time increments, the incremental fluid volumes produced, and the instantaneous flow rates and resistance to flow in the core sample. The system 60 checks the acquired data against internal requirements to see whether or not the conditions are proper for utilizing the acquired data. If not, it checks to see if an end of run command has been received and if no end of run command has been received it is cycled back to the beginning of the flow chart of FIG. 29. Otherwise, the program ends. However, if the conditions are proper and they meet the incremental time and volume conditions, the system then plots the cumulative produced oil and resistance on the screen and writes the data to the disk file. This cycle comprises the acquisition of a single data point. The system 60 then updates the time and cumulative volume requirements so that data acquisition is based on a logarithmic distribution of cumulative volume. The system then cycles back to the beginning of the flow chart of FIG. 29 to await the next data point.

Figure 30:
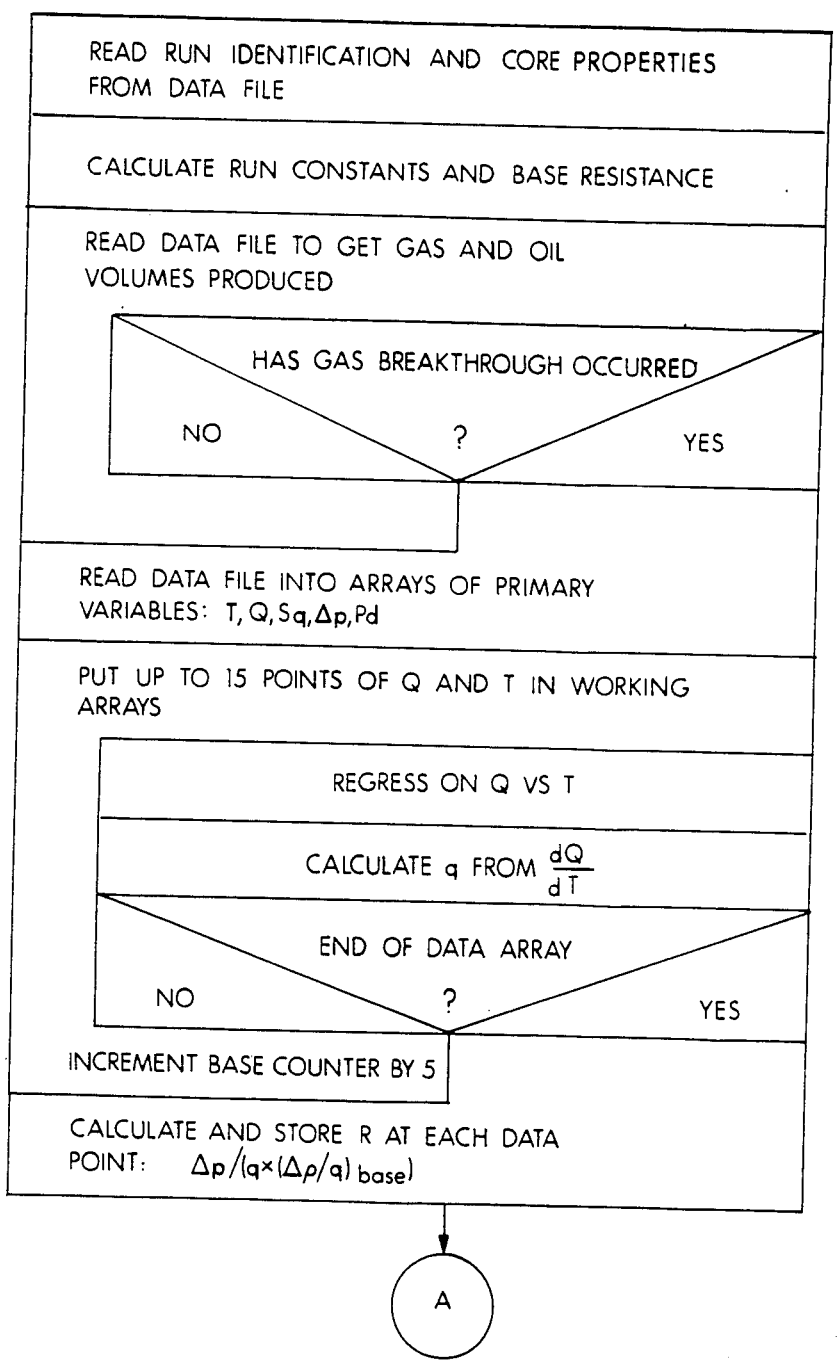

In FIG. 30, the system 60 reads the run identification and core properties from the data file which was stored in the flow chart of FIG. 29. The system then calculates the run constants and base resistance. The run constants are values such as core sample cross sectional area, and pore volume, and viscosity times core length divided by the product of core permeability and area. It then proceeds to read the data file and to obtain the gas and the oil volumes produced. The system 60 then makes a determination as to whether or not gas breakthrough has occurred. If not, it discards the present data point and cycles. Gas breakthrough is the point at which injected gas first reaches the outlet face of the core. Following breakthrough, two phase flow conditions exit. However, if gas breakthrough has occurred, then the system reads the data file into arrays of primary variables: T, Q, Sg, delta P, and PD where each of these variables is defined as follows:

T is the elapsed time in seconds from the point picked as breakthrough, or from the start of injection.

Q is the cumulative volume of gas injected at each port converted to the mean pressure in the core.

Sg is the average gas saturation in the core. It is numerically equal to the volume of oil produced from the core divided by the pore volume of the sample.

Pd is the differential pressure across the sample at each data point, in psi.

The system then takes up to fifteen readings of Q v. T into its working arrays and then proceeds to regress on Q v. T.

In this procedure a 3rd order polynomial equation is fitted in a least squares sense to the data set of up to 15 points. From the polynomial least squares regression the constants defining the equation of the line are found. By overlapping the data sets in groups of 5 points some smoothing is achieved, along with better consistency of results. Using the equation of the line formed during regression, numerical differentiation is applied to find derivatives at each data point.

The system then calculates the q from the dQ/dT then ascertains whether or not the data array is complete. If not, the system cycles and if so, the system calculates and stores R at each data point where R is determined as follows:

$$R = \Delta p/(q \times (\Delta p/q)_{base})$$

Figure 31:
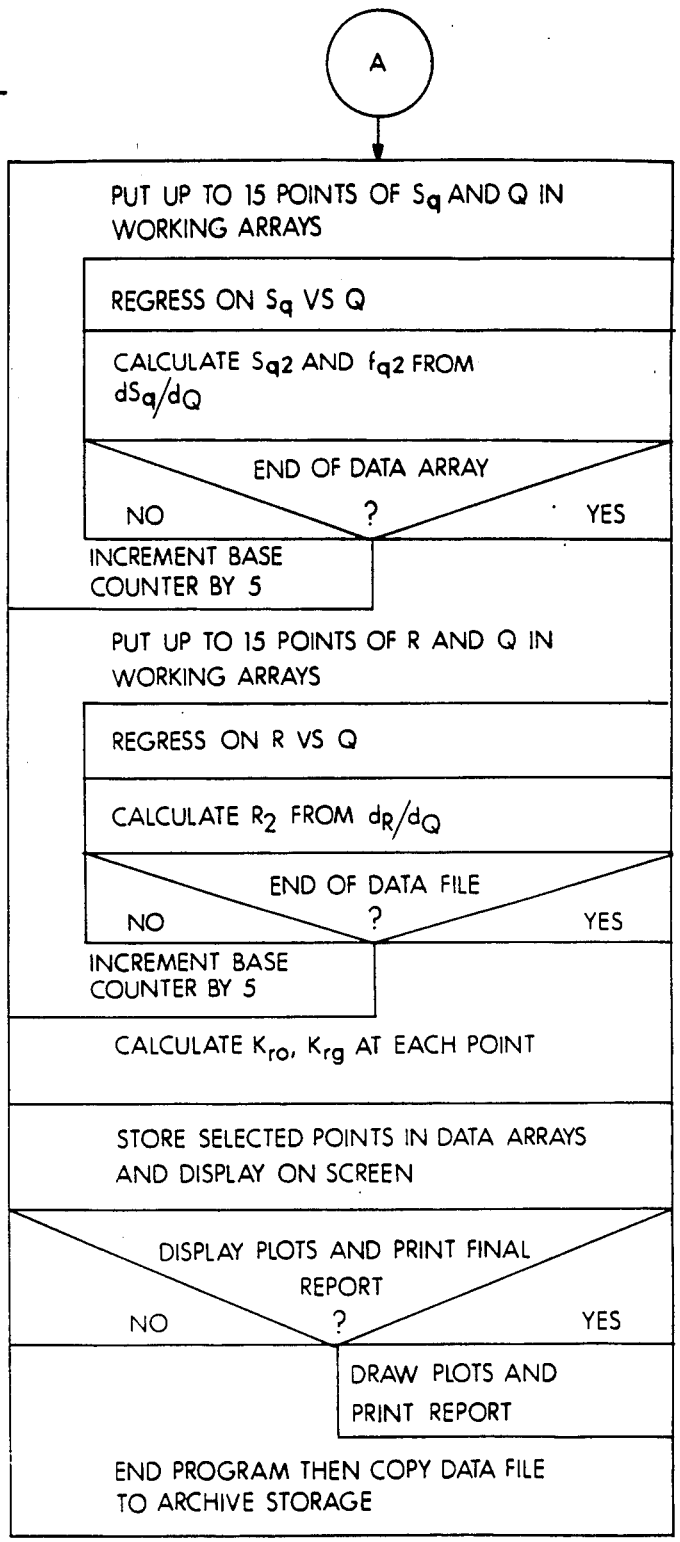

In FIG. 31, the system continues to read at most fifteen values of Sg and Q in working arrays. The system then regresses on Sg v. Q. This procedure is similar to that discussed above, whereby a 3rd order polynomial equation is fitted to the data set of Sg v. Q. Derivatives of the resultant equation are then calculated at each point.

Figure 32:
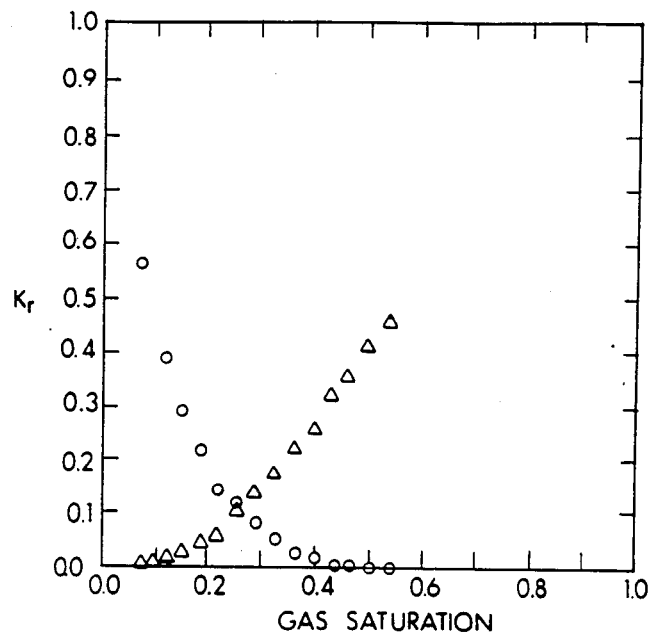
FIGS. 32 and 33 are graphical illustrations of the computer 60 output of the present invention.
Figure 33:
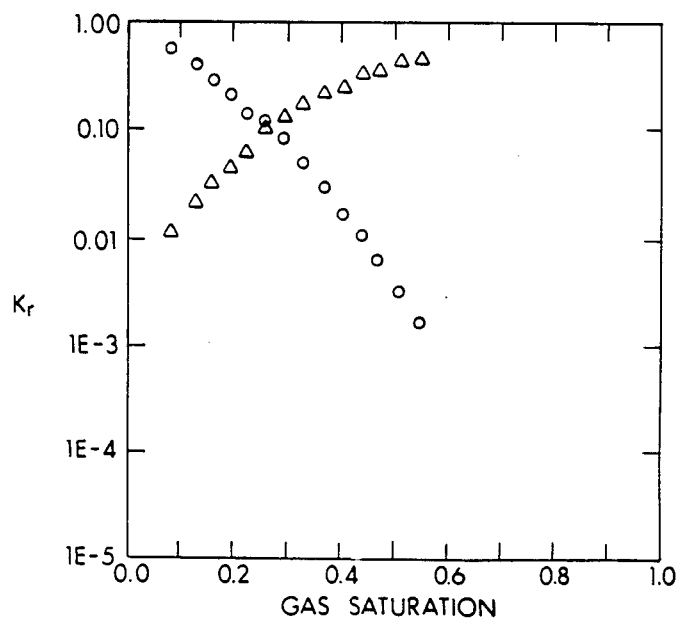

The system then calculates Sg2 and fg2 from dSg/dQ. The system cycles until the array is complete and then it generates at most fifteen points of R and Q in working arrays. The system regresses on R v. Q as above so that an equation is generated fitting the data in a least squares sense and then calculates R2 from dR/dQ and continues until the end of this file is produced. If so, the system calculates the Kro, Krg at each data point. It then proceeds to store the selected points of data in arrays and displays it on the screen. When it is complete, it draws the plots and prints the report. An example of the plots are shown in FIGS. 32 and 33 and an example of the data printed on the report is shown below:

| Sg | Krg | Kro | Fg | PVi |
|---|---|---|---|---|
| 0.0494 | 0.0070 | 0.6293 | 0.3344 | 0.2 |
| 0.0804 | 0.0119 | 0.5461 | 0.4953 | 0.2 |
| 0.1324 | 0.0216 | 0.4174 | 0.6999 | 0.3 |
| 0.1773 | 0.0328 | 0.3124 | 0.8253 | 0.4 |
| 0.2125 | 0.0457 | 0.2248 | 0.9015 | 0.6 |
| 0.2467 | 0.0669 | 0.1721 | 0.9459 | 1.0 |
| 0.2794 | 0.0949 | 0.1408 | 0.9681 | 2.0 |
| 0.3110 | 0.1180 | 0.1063 | 0.9804 | 3.2 |
| 0.3430 | 0.1439 | 0.0768 | 0.9883 | 5.2 |
| 0.3763 | 0.1715 | 0.0517 | 0.9933 | 8.8 |
| 0.4073 | 0.2027 | 0.0363 | 0.9960 | 15.6 |
| 0.4437 | 0.2379 | 0.0237 | 0.9978 | 27.8 |
| 0.4857 | 0.2783 | 0.0136 | 0.9989 | 49.9 |
| 0.5198 | 0.3164 | 0.0080 | 0.9994 | 88.3 |
| 0.5585 | 0.3729 | 0.0043 | 0.9997 | 187.1 |
| 0.5941 | 0.4391 | 0.0024 | 0.9999 | 393.3 |
| 0.6309 | 0.5111 | 0.0013 | 0.9999 | 823.8 |

-continued

| Sg | Krg | Kro | Fg | PVi |
|---|---|---|---|---|
| 0.6668 | 0.5862 | 0.0006 | 1.0000 | 1718.1 |

Ka = 714.0 md
Phi = 0.172
Swc = 0.000
L = 7.698 cm
D = 2.525 cm
ps = 600.0 psi

The data printed on the report include sample identification parameters such as core absolute permeability, Ka; porosity, Phi; water saturation present in the core, SWc; core length, L; diameter, D; and pressure applied to the sleeve of the Hassler core holder, Ps. Data resulting from the calculations are presented in tabulation form as follows:

Sg=gas saturation value corresponding to the reported relative permeabilities.

Kg=relative permeability to gas at each saturation, referenced to the Ka shown above.

Kro=relative permeability to oil.

Fg=fractional flow of gas, defined as gas flow rate divided by total instantaneous flow rate at each saturation.

PVi=pore volume of gas injected to reach each saturation. The value is connected to the mean flowing pressure in the core so that compression of the gas volume is accounted for.

The foregoing description of the invention has been presented for purposes of illustration and description. The foregoing description is not intended to be exhaustive or to limit the invention to the precise form disclosed, and other modifications and variations may be possible in light of the above teachings. The embodiment was chosen and described in order to best describe the principles of the invention and its practical application to thereby enable others skilled in the art to best utilize the invention in various embodiments and various modifications as are suited to the particular use contemplated. It is intended that the appended claims be construed to include other alternative embodiments in the invention except in so far as limited by the prior art.

I claim:

1. An automated gas-liquid relative permeameter for determining the relative permeability of a core sample, said permeameter comprising:

means (40) for providing a vacuum, means (30) for providing a supply of helium gas, means (20) for providing a supply of nitrogen gas, means (80) connected to said vacuum and nitrogen providing means for holding said core at a predetermined pressure, means (120) engaging the top of said core and connected to said holding means for applying said predetermined pressure to said top of said core, means (70) cooperative with said applying means and connected to said helium providing means and said nitrogen providing means for supplying said helium gas to said top of said core under control of said nitrogen gas, means (100) engaging the bottom of said core and removably connected to said holding means for delivering said predetermined pressure to said bottom of said core, means (90) cooperative with said delivering means for collecting produced liquid from said core sample when said helium gas is supplied to said top of said core by said supply means, means (240) engaging said produced liquid collecting means for instantaneously weighing said collected fluid, means (110) cooperative with said delivering means for collecting produced helium gas from said core sample when said helium gas is supplied to said top of said core by said supplying means, means (258) connected to said produced helium collecting means for instantaneously measuring the pressure of said collected helium gas, and means (60) connected to said weighing means and to said measuring means for automatically determining said gas-liquid relative permeability of said core sample.

2. the permeameter of claim 1 in which said applying means is a hydraulic ram.

3. The permeameter of claim 1 in said supplying means comprises means receptive of said nitrogen gas from said nitrogen providing means for sealing said top of said core sample, said sealing means upon removal of said nitrogen gas being capable of delivering said helium gas to said top of said core sample.

4. The permeameter of claim 3 in which said sealing means comprises:

a piston, said helium gas being delivered under said piston, a shaft connected under said piston, a plug connected to the end of said shaft opposing said piston, said plug sealing said top of said core sample when nitrogen gas is delivered to the top of said piston and said plug uncovering said top of said core sample when said nitrogen gas is removed from said top of said piston.

5. The permeameter of claim 1 in which said delivering means is an elevator.

6. The permeameter of claim 1 in which said produced liquid collecting means comprises:

a collection tube, means connected to said delivering means for centering said tube under said bottom of said core sample, means receptive of said produced helium gas and said produced liquid for directing said helium gas and said produced liquid into collection tube, said collection tube receiving said produced liquid, and means engaging said collection tube and receptive of said produced helium gas for removing said helium gas from said collection tube.

7. The permeameter of claim 6 in which said collection tube is removable from said produced liquid collecting means when said delivering means is in a lowered position.

8. The permeameter of claim 6 in which said collection tube has a downwardly extending pin oriented in the bottom center of said collection tube and in which said weighing means comprises a load cell engaging said pin.

9. The permeameter of claim 1 in which said weighing means is a load cell.

10. The permeameter of claim 1 in which said produced helium collecting means comprises:

at least one tank for storing said produced gas, and means connected to said at least one tank for measuring the pressure of said produced gas, said measuring means being connected said determining means.

11. An automated gas-liquid relative permeameter for ascertaining the relative permeability of a core sample, said permeameter comprising:

means for providing a supply of gas, means for holding said core sample at a predetermined pressure, means engaging the top of said core sample and connected to said holding means for applying said predetermined pressure to said top of said core sample, means cooperative with said applying means and connected to said gas providing means for selectively supplying said gas to said top of said core sample, means engaging the bottom of said core sample and releasably connected to said holding means for delivering said predetermined pressure to said bottom of said sample core, means cooperative with said delivering means for collecting produced liquid from said core sample when said gas is supplied to said top of said core sample by said supplying means, means engaging said produced liquid collecting means for instantaneously weighing said collected fluid, means cooperative with said delivering means for collecting produced gas from said core sample when said gas is supplied to said top of said core by said supplying means, means connected to said produced gas collecting means for instantaneously measuring the pressure of said collected gas, and means connected to said weighing means and to said measuring means for automatically determining said gas-liquid permeability of said core sample bases on said instantaneous weight of said fluid and on said instantaneous pressure of said gas.

12. The permeameter of claim 11 in which said applying means is a hydraulic ram.

13. The permeameter of claim 11 in which said supplying means comprises means interconnected with said determining means for automatically sealing said top of said core sample, said sealing means being further capable of automatically delivering said gas to said top of said core sample under control of said determining means.

14. The permeameter of claim 13 in which said sealing means comprises:

a piston, said gas being delivered under said piston, a shaft connected under said piston, a plug connected to the end of said shaft opening said piston, said plug sealing said top of said core sample to prevent said gas from entering said core sample, said determining means activating said piston to uncover said top of said core sample so that said helium gas under said piston is delivered into said top of said core sample.

15. The permeameter of claim 11 in which said delivering means is an elevator.

16. The permeameter of claim 11 in which said produced liquid collecting means comprises:

a collection tube, means connected to said delivering means for centering said tube under said bottom of said core sample, means receptive of said produced gas and said produced liquid for directing said produced gas and said produced liquid into collection tube, said collection tube receiving said produced liquid, and means engaging said collection tube and receptive of said produced gas for removing said gas from said collection tube.

17. The permeameter of claim 16 in which said collection tube is removable from said produced liquid collecting means when said delivering means is in a lowered position.

18. The permeameter of claim 16 in which said collection tube has a downwardly extending pin oriented in the bottom center of said collection tube and in which said weighing means comprises a load cell engaging said pin.

19. The permeameter of claim 11 in which said weighing means is a load cell.

20. The permeameter of claim 11 in which said produced gas collecting means comprises:

at least one tank for storing said produced gas, and means connected to said at least one tank for measuring the pressure of said produced gas, said measuring means being connected to said determining means.

21. An automated gas-liquid relative permeameter for ascertaining the relative permeability of a core sample held under a predetermined pressure, said permeameter comprising:

means for providing a supply of gas, means engaging the top of said core sample and connected to said gas providing means for selectively supplying said gas to said top of said core sample, first means engaging the bottom of said core sample for collecting produced liquid from said core sample when said gas is supplied to said top of said core sample by said supplying means, means engaging said first collecting means for instantaneously weighing said collected fluid, second means engaging the bottom of said core sample for collecting produced gas from said core sample when gas is supplied to said top of said core by said supplying means, means connected to said second collecting means for instantaneously measuring the pressure of said collected gas, and means connected to said weighing means and to said measuring means for automatically determining said gas-liquid permeability of said core sample based on said instantaneous weight of said fluid and on said instantaneous pressure of said gas.

22. An automated gas-liquid relative permeameter for ascertaining the relative permeability of a core sample held under a predetermined pressure, said permeameter comprising:

a computer, means for providing a supply of gas, means engaging the top of said core sample and connected to said gas providing means for supplying said gas to said top of said core sample, first means engaging the bottom of said core sample for collecting produced liquid from said core sample when said gas is supplied to said top of said core sample by said supplying means, means engaging said first collecting means and connected to said computer for instantaneously weighing said collected fluid, second means engaging the bottom of said core sample for collecting produced gas from said core sample when said gas is supplied to said top of said core by said supplying means, means connected to said second collecting means and to said computer for instantaneously measuring the pressure of said collected gas, and said computer being further capable of automatically determining said gas-liquid permeability of said core sample based on said instantaneous weight of said fluid and on said instantaneous pressure of said gas.

23. An apparatus for instantaneously weighing the produced liquid from a core sample during a permeability test, said apparatus comprising:

means engaging the bottom of said core sample during said test for collecting said produced liquid, means centering said collecting means under said core sample for releasably holding said collecting means, and means connected to said holding means and supporting said collecting means for issuing a signal proportional to the instantaneous weight of said produced liquid in said collecting means.

24. The apparatus of claim 23 in which said collecting means is a collection tube.

25. The apparatus of claim 23 in which said issuing means is a load cell.

26. The apparatus of claim 23 in which said issuing means is a load cell, a collection tube for collecting said produced liquid from said core sample during said test, said collection tube having a downwardly extending pin oriented in the bottom center of said collection tube, means centering said collection tube under said core sample for releasably holding said collection means, and a load cell mounted to said holding means and engaging said pin from said collection tube for issuing an electrical signal proportional to the instantaneous weight of said produced liquid in said collection tube means.

27. An apparatus for instantaneously determining the pressure of the produced gas from a core sample during a relative permeability test, said apparatus comprising:

means engaging the bottom of said core sample during said test for collecting said produced gas from said core sample, and means connected to said collecting means for issuing a signal proportional to the instantaneous pressure of said produced gas in said collecting means.

28. An apparatus for instantaneously determining the pressure of the produced gas from a core sample during a relative permeability test, said apparatus comprising:

a regulator, means engaging the bottom of said core sample during said test for delivering said produced gas to said regulator, at least one tank connected to said regulator for storing said delivered gas from said delivering means when said delivered gas exceeds a predetermined value in said regulator, and means connected to said at least one tank for issuing a signal proportional to the instantaneous pressure of said produced gas in said at least one tank.

29. The apparatus of claim 28 wherein said at least one tank comprises two tanks and further comprises means between said two tanks for selectively switching between storing said produced gas in one tank while venting the second tank to atmosphere.

30. An apparatus for instantaneously determining the weight of the produced liquid and the pressure of the produced gas from a core sample during a relative permeability test, said apparatus comprising:

first means engaging the bottom of said core sample during said test for collecting said produced liquid, second means engaging the bottom of said core sample during said test for collecting said produced gas from said core sample, means connected to said first collecting means for issuing a signal proportional to the instantaneous weight of said produced liquid in said first collecting means, and means connected to said second collecting means for issuing a signal proportional to the instantaneous pressure of said produced gas in said second collecting means.

31. The apparatus of claim 30 in which said first collecting means is a releasable collection tube.

32. The apparatus of claim 30 in which said issuing means is a load cell, said load being capable of issuing an electrical signal proportional to said instantaneous weight.

33. The apparatus of claim 30 further comprising means receptive of said instantaneous pressure and weight signals for determining said instantaneous pressure and said instantaneous weight.

34. An automated gas-liquid relative permeameter for ascertaining the relative permeability of a core sample held under a predetermined pressure, said permeameter comprising:

a computer, means for providing a supply of gas, means engaging the top of said core sample and connected to said gas providing means for supplying said gas to said top of said core sample, first means engaging the bottom of said core sample for collecting produced liquid from said core sample, means engaging said first collecting means and connected to said computer for instantaneously weighing said collective fluid, second means engaging the bottom of said core sample for collecting produced gas from said core sample, means connected to said second collecting means and to said computer for instantaneously measuring the pressure of said collected gas, means connected across said core sample and to said computer for instantaneously measuring the differential pressure of said gas across said core sample, means engaging the bottom of said core sample and connected to said computer for measuring the down stream pressure of said produced gas from said core sample, and said computer being further capable of automatically determining said gas-liquid relative permeability of said core sample based upon said instantaneous weight of said fluid, the instantaneous differential pressure of said gas, the said instantaneous down stream pressure of said produced gas, and the instantaneous pressure of said collected gas.

* * * * *

UNITED STATES PATENT AND TRADEMARK OFFICE
CERTIFICATE OF CORRECTION

PATENT NO. : 4,679,421

DATED : July 14, 1987

INVENTOR(S) : Robert D. Barree

It is certified that error appears in the above-identified patent and that said Letters Patent are hereby corrected as shown below:

Col. 7, line 14:   Delete "prot" and insert --port--.
Col. 7, line 47:   Delete "packaye" and insert --package--.
Col. 8, line 3:    Delete "611" and insert --622--.
Col. 16, line 19:  Delete "in said" and insert --in which said--.

Signed and Sealed this

Tenth Day of November, 1987

Attest:

DONALD J. QUIGG

Attesting Officer

Commissioner of Patents and Trademarks